United States Patent [19]

Mamone et al.

[11] Patent Number: 5,744,312

[45] Date of Patent: Apr. 28, 1998

[54] **THERMOSTABLE DNA POLYMERASE FROM *THERMOANAEROBACTER THERMOHYDROSULFURICUS***

[75] Inventors: Joseph A. Mamone, Parma; Maria Davis, Twinsburg; Dan Sha, Euclid, all of Ohio

[73] Assignee: Amersham Life Science, Inc., Cleveland, Ohio

[21] Appl. No.: 766,014

[22] Filed: Dec. 13, 1996

Related U.S. Application Data

[60] Provisional application No. 60/008,688 Dec.15, 1995.
[51] Int. Cl.[6] .............................. C12N 9/12; C12N 15/54; C12P 19/34; C12Q 1/68
[52] U.S. Cl. .................. 435/6; 435/91.1; 435/91.2; 435/252.3; 435/194; 435/325; 435/419; 536/23.2
[58] Field of Search .................. 435/194, 6, 91.1, 435/91.2, 252.3, 325, 419; 536/23.2

[56] References Cited

U.S. PATENT DOCUMENTS

| | | | |
|---|---|---|---|
| 4,683,195 | 7/1987 | Mullis et al. | 435/6 |
| 4,889,818 | 12/1989 | Gelfand et al. | 435/194 |
| 5,173,411 | 12/1992 | Tabor et al. | 435/91 |

FOREIGN PATENT DOCUMENTS 0655506  5/1995  European Pat. Off. .

OTHER PUBLICATIONS

Joyce and Steitz, "Function and Structure Relationships in DNA Polymerases," *Annu. Rev. Biochem*, 63:777–822 (1994).

Kong et al., "Characterization of a DNA Polymerase from the Hyperthermophile Archaea *Thermococcus litoralis*," *J. Biol. Chem.* 268:1965–1975 (1993).

Reddy et al., "Hyperexpression and purification of *Escherichia coli* adenylate cyclase using a vector designed for expression of lethal gene products," *Nucleic Acids Research* 17:10473–10488 (1989).

Richardson, "DNA polymerase from *Escherichia coli*," *Procedures in Nucleic Acid Research*, Cantoni and Davies editors, Harper and Row, New York, pp. 263–276 (1966).

Scopes, *Protein Purification*, Springer–Verlag, New York, New York, pp. 46–48 (1994).

Uemori et al., "Cloning of the DNA Polymerase Gene of *Bacillus caldotenax* and Characterization of the Gene Product," *J. Biochem.* 113:401–410 (1993).

Walker et al., "Isothermal in vitro amplification of DNA by a restriction enzyme/DNA polymerase system," *Proc. Natl. Acad. Sci. USA* 89:392–396 (1992).

*Primary Examiner*—Keith D. Hendricks
*Attorney, Agent, or Firm*—Lyon & Lyon LLP

[57] ABSTRACT

An enzymatically active DNA polymerase or fragment thereof having at least 80% homology in its amino acid sequence to at least a contiguous 40 amino acid sequence of the DNA polymerase of *Thermoanaerobacter thermohydrosulfuricus*.

33 Claims, 17 Drawing Sheets

```
CTGCAGAAAAAAATAATAAAAAGTTTAAAAAATATGCCTCCTATAGAACTTCC
TGAAGATTTTAATAAAAAATTACATCA
AAAATTGATTTATCATAAAAATTTTTTAGAGAAGAAAAAAGAAAGGCTAAAAA
AGACGTTTAACAATAGTAGCTATTGCG
ACATCTTTAATATTTATGACAGTATTTATAGTGAATACATTTAATAAATCCTTA
CAAATTGAGTCTAATACTCCTTTAGC
TAACATTGAAATGGGACAGAGTTATGGCTTACCTCAGAAAGAAGGAGCTAATA
ATGAAAGAGGATTGCCAGCAGGAACTT
CAAGGAAAATTACAAAGAATGCAACCATTTCCTTGGAAGTAGAAGACGTCAAT
GGATGTTATGATAAAGTCTTTCAGTTA
GTAAAAGAAGCAGAAGGTTTTATTGAAACTTCTGAGGAAACAGTATCCAGTGA
TAATATCAAAAGGGTAAATGTTGTTTT
GAAGGTGCGGGAAGATAAATTTGAAAGTGTGATTTCTCAAATTAAAGATTTGG
CAAAGTAACAGCTTTAAGGATTGACAG
CAAAGACATTACAGACCAGTATTATGACTTACAAGCAAGGCTAAAAAATTTGG
AAGTAGAGGAACAAAAGCTTCAAGACA
TCATGAATAAGGCTACTACAGTCAAGGAAATGCTTGAAGTAGAATCTGAAATA
AACAGGATAAGAAGTGAAATAGAGTCA
ATGGAAGGACAGCTAAAATTATGGGAAAATCTTACGAGTCTGGCAACCATAAA
TCTTTCAATAAAAGAGATACCTAAAGA
TGAGAAACCTTTGGCTATAGTTTCTTTTAAGGGAATTGGTAAAGGTATAAAAG
AAGCATTTATAAATAATATGAATTTTT
TAATATTTTTTATGAAAAGTTGATAATAATATTGGTGATAATTTTGCCTTATA
GTGTACTGGCTTTAATCGGTTATAAA
GTGTATATCTATTTCAAAAAAAGGAGATGACAATTTACATCTTCTTTTTTTGC
GGTATATTAAAATACAAAGAAATAAA
AATGGGAGTGATTTAATGTATAAATTTTTAATAATTGATGGAAGTAGCCTCATG
```

*FIG. 1A*

```
TACAGAGCCTATTATGCCTTGCCCAT
GCTTACTACAAGTGAGGGATTGCCTACAAATGCTCTGTATGGTTTTACTATGAT
GCTTATAAAACTTATCGAGGAGGAAA
AACCTGATTACATAGCTATTGCTTTTGACAAAAAGCTCCTACTTTTAGACACA
AAGAATATCAAGACTACAAAGCTACA
AGACAAGCTATGCCTGAAGAACTTGCTGAACAAGTAGACTATTTGAAAGAAAT
TATAGATGGCTTTAATATAAAGACATT
AGAATTAGAAGGTTATGAAGCTGATGACATTATAGGGACTATTTCAAAGCTGG
CAGAGGAAAAAGGAATGGAAGTGCTTG
TAGTTACAGGAGACAGAGATGCTCTTCAATTAGTTTCAGATAAAGTGAAGATA
AAAATTTCTAAAAAGGGTATTACTCAG
ATGGAAGAGTTTGACGAAAGGCTATTTTAGAAAGGTATGGAATAACTCCTCA
GCAGTTTATAGATTTAAAAGGGCTTAT
GGGAGATAAATCTGATAATATCCCTGGAGTACCTAATATAGGGGAAAAAACTG
CGATTAAGCTATTAAAGGATTTTGGAA
CAATTGAAAATTTAATCCAAAATCTTTCTCAGCTTAAAGGTAAAATAAAAGAA
AATATAGAAAACAATAAAGAGTTAGCT
ATAATGAGTAAGAGGCTTGCTACTATAAAAAGAGACATTCCCATTGAGATAGA
TTTTGAGGAGTATAAAGTAAAAAAATT
.TAATGAGGAGAAGCTTTTAGAGCTTTTTAATAAATTAGAATTCTTTAGTTTAAT
TGATAACATAAAGAAAGAAAGTAGCA
TAGAGATTGTAGATAATCATAAAGTTGAAAAATGGTCAAAAGTAGATATAAAA
GAATTAGTAACTTTGTTGCAAGATAAC
AGAAATATTGCTTTTTACCCGTTAATTTATGAAGGGGAATAAAAAAAATAGC
CTTTTCTTTTGGAAAGGATACGGTTTA
TATTGACGTTTTCCAAACAGAAGATTTAAAGGAGATTTTTGAAAAGAAGATT
TTGAATTTACAACCCATGAAATAAAGG
ATTTTTTAGTGAGGCTTTCTTATAAAGGAATAGAGTGTAAAAGCAAGTACATA
GATACTGCTGTAATGGCTTATCTTCTG
```

*FIG. 1B*

AATCCTTCTGAGTCTAACTATGACTTAGACCGTGTGCTAAAAAATATTTAAAG
GTAGATGTGCCTTCTTATGAAGGAAT
ATTTGGCAAAGGTAGGGATAAAAAGAAAATTGAAGAGATTGACGAAAACATA
CTTGCTGATTATATTTGCAGTAGATGTG
TGTATCTATTTGATTTAAAAGAAAAGCTGATGAATTTTATTGAAGAGATGGATA
TGAAAAAACTTCTATTAGAAATAGAA
ATGCCTCTTGTAGAAGTTTTAAAATCAATGGAGGTAAGTGGTTTTACATTGGAT
AAAGAAGTTCTAAAAGAGCTTTCACA
AAAGATAGATGATAGAATAGGAGAAATACTAGATAAAATTTATAAAGAGGCA
GGATATCAATTTAATGTAAATTCACCTA
AGCAATTAAGTGAATTTTTGTTTGAAAAGTTAAACTTACCAGTAATAAAGAAA
ACAAAAACAGGATACTCTACGGATTCT
GAAGTTTTGGAACAATTGGTTCCTTATAATGATATTGTCAGCGATATAATAGAG
TATCGGCAACTTACAAAACTTAAATC
TACTTATATAGATGGATTTTTGCCTCTTATGGATGAAAACAATAGAGTACATTC
TAATTTTAAACAAATGGTTACTGCTA
CAGGTAGAATAAGCAGCACCGAGCCAAATCTACAAAATATACCTATAAGAGA
AGAGTTTGGCAGACAAATTAGAAGGGCT
TTTATTCCGAGGAGTAGAGATGGATATATTGTTTCAGCAGATTATTCTCAGATT
GAACTGAGGGTTTTAGCACATGTTTC
GGGAGATGAAAAGCTAATAGAATCTTTTATGAATAATGAAGATATACATTTAA
GGACAGCTTCGGAGGTTTTTAAAGTTC
CTATGGAAAAAGTTACACCGGAGATGAGAAGAGCAGCAAAAGCCGTAAATTT
TGGCATAATATATGGCATAAGCGATTAT
GGGCTTTCTCGAGACCTTAAAATATCAAGAAAAGAAGCAAAAGAGTACATAA
ATAATTATTTTGAAAGATATAAAGGAGT
AAAAGATTATATTGAAAAAATAGTACGATTTGCAAAAGAAAATGGCTATGTGA
CTACAATAATGAACAGAAGGAGATATA

*FIG. 1C*

```
TTCCTGAAATAAACTCAAGAAATTTTACTCAAAGATCGCAGGCCGAAAGGTTA
GCAATGAATGCTCCGATACAGGGAAGT
GCGGCTGATATAATAAAAATGGCAATGGTTAAGGTATACAACGATTTAAAAAA
ATTAAAGCTTAAGTCTAAGCTTATATT
GCAAGTTCATGACGAGCTTGTAGTGGATACTTATAAGGATGAAGTAGATATCA
TAAAAAAGATACTTAAAGAAAATATGG
AAAATGTAGTGCAATTAAAAGTTCCTCTGGTTGTTGAAATTGGCGTAGGGCCT
AATTGGTTTTTGGCCAAGTGAGGTGTG
CAAAAATGCAAGTAATTGGACTTACTGGCGGCATTGCCTCAGGTAAAAGTACT
GTATCCAAGCTATTAAAAAGATGGGA
GCTGTGGTAATTGATGCAGATATTGTATCAAGAGAAATAATGGTAAAAGGAAC
AGAAGCATATAATAGAATTGTAGAATA
TTTTGGAAAAGAAATTTTAAAGGAAGACGGCGAAATTGACAGAAAGAAATTA
GGCAATATTGTGTTTGCTGACAGAAAA
AGCTTAAAAAACTAAATGAAATTACTCATCCCATAATAATAGAGAGGATAAAA
GAAAAAATAGAAGAAGAAAGAAAAAAA
ATCAGCAAAAGGCAATTGTATTAGATGCAGCTCTTTTAATTGAGATGAACTTTA
TAAATGGTAGATGAGGTTTGGTTAGT
AGTAGTAGACTCAAAAACTCAAATAAAGAGGGTTATGGAGAGGGATAAGCTTT
CTTATAAGGATGCGATAAACCGAATAA
AAAGCCAAATGCTTTGGACGAAAAAATGAAGTACGCAGATTTTATAATAAACA
TAGCAAAGTTTTAAAGCTATGGAAAAA
CAGTTACACTATTTTGGGAAAGATTGCAACGTAAATTCATGATATCGGAGGA
GTTACTTTGAGAAAAAAGTTGCGGCA
ATTTTAATACTATTAAGTTTATTGTTTACTTACGAGTTAAATACTCATTATTTTT
TAAAAAAAATTTATCCTCGTAAATA
CTATAATTATGTATTTTATTACGCAAAGAGTATGGCATGGACCCCTATCTTAT
TTTTGCTGTGATAAAAGTCGAAAGTA
ATTTTAGAAGCGATGCAATTTCCAGCAAAAATGCTAGAGGGTTAATGCAAATT
```

*FIG. 1D*

TTACCAGAAACTGGAGAATGGATTGCT
AAAGAAATAGGGATAAAAATTACAGCAATAGTATGCTTTTTGAACCTAAATA
TAATATTCAAATGGGAACGTGGTATTT
GACTTATCTTCTTAAAACTTTTAATGGAAATATTAAATTGGCTCTAGCGGCCTA
TAACGGAGGCAGTGGAAATGTAGATG
CATGGCTTAAAGATAAAAGATTTTCTAAAGATGGTAAACAACTACATATTGTT
CCTTTTCCTGAGACAAATAAATATATA
AAAAAGGTATTAGCAGTTTACGAGATCTATAAGTTCATATATGAAACTAAGAA
TTGATATGAAGATTACTATATACAAAA
AAAGTTGAAAAATTGGTATAATAGTATCGTTAAAAAGAAAATAAAAAGGGAG
GACACAAATGAAACCGTTGAAACATTTA
AAAGACTTAAAGGAAGTAAAAATCGAAAGAGATAGGGAGTTTTTCTCAGCCAC
TCATGAAGAAATAAAAAATGCTTGGAC
TACAGATGTGTATTTTTAAGAACCCAAGATATTTATCATATCTTGGTGTACA
GGATAAAATAGTTACTGCAGAGATAT
TTCCAAGAAAAAAGGAGTTTTTGCAGGATTACCAGAAGTAATGAGTTTACTT
AAAGACAAAAATGTGGAAGTATGGTCT
TTGAAAGAAGGAGATACTTTTGAAGCTAAAGATACGGTAATGAGAATAAAAG
GACCTTATAGTGAATTTGGAATTTATGA
AACGGCAATATTAGGAATTC

FIG. 1E

```
1/1                                  31/11
ATG TAT AAA TTT TTA ATA ATT GAT GGA AGT AGC CTC ATG TAC AGA GCC TAT TAT GCC TTG
 M   Y   K   F   L   I   I   D   G   S   S   L   M   Y   R   A   Y   Y   A   L
61/21                                91/31
CCC ATG CTT ACT ACA AGT GAG GGA TTG CCT ACA AAT GCT CTG TAT GGT TTT ACT ATG ATG
 P   M   L   T   T   S   E   G   L   P   T   N   A   L   Y   G   F   T   M   M
121/41                               151/51
CTT ATA AAA CTT ATC GAG GAG GAA AAA CCT GAT TAC ATA GCT ATT GCT TTT GAC AAA AAA
 L   I   K   L   I   E   E   E   K   P   D   Y   I   A   I   A   F   D   K   K
181/61                               211/71
GCT CCT ACT TTT AGA CAC AAA GAA TAT CAA GAC TAC AAA GCT ACA AGA CAA GCT ATG CCT
 A   P   T   F   R   H   K   E   Y   Q   D   Y   K   A   T   R   Q   A   M   P
241/81                               271/91
GAA GAA CTT GCT GAA CAA GTA GAC TAT TTG AAA GAA ATT ATA GAT GGC TTT AAT ATA AAG
 E   E   L   A   E   Q   V   D   Y   L   K   E   I   I   D   G   F   N   I   K
301/101                              331/111
ACA TTA GAA TTA GAA GGT TAT GAA GCT GAT GAC ATT ATA GGG ACT ATT TCA AAG CTG GCA
 T   L   E   L   E   G   Y   E   A   D   D   I   I   G   T   I   S   K   L   A
361/121                              391/131
GAG GAA AAA GGA ATG GAA GTG CTT GTA GTT ACA GGA GAC AGA GAT GCT CTT CAA TTA GTT
 E   E   K   G   M   E   V   L   V   V   T   G   D   R   D   A   L   Q   L   V
421/141                              451/151
TCA GAT AAA GTG AAG ATA AAA ATT TCT AAA AAG GGT ATT ACT CAG ATG GAA GAG TTT GAC
 S   D   K   V   K   I   K   I   S   K   K   G   I   T   Q   M   E   E   F   D
481/161                              511/171
GAA AAG GCT ATT TTA GAA AGG TAT GGA ATA ACT CCT CAG CAG TTT ATA GAT TTA AAA GGG
 E   K   A   I   L   E   R   Y   G   I   T   P   Q   Q   F   I   D   L   K   G
541/181                              571/191
CTT ATG GGA GAT AAA TCT GAT AAT ATC CCT GGA GTA CCT AAT ATA GGG GAA AAA ACT GCG
 L   M   G   D   K   S   D   N   I   P   G   V   P   N   I   G   E   K   T   A
601/201                              631/211
ATT AAG CTA TTA AAG GAT TTT GGA ACA ATT GAA AAT TTA ATC CAA AAT CTT TCT CAG CTT
 I   K   L   L   K   D   F   G   T   I   E   N   L   I   Q   N   L   S   Q   L
661/221                              691/231
AAA GGT AAA ATA AAA GAA AAT ATA GAA AAC AAT AAA GAG TTA GCT ATA ATG AGT AAG AGG
```

FIG. 2A

```
                  K  G  K  I  K  E  N  I  E  N  N  K  E  L  A  I  M  S  K  R
721/241                                          751/251
CTT GCT ACT ATA AAA AGA GAC ATT CCC ATT GAG ATA GAT TTT GAG GAG TAT AAA GTA AAA
 L   A   T   I   K   R   D   I   P   I   E   I   D   F   E   E   Y   K   V   K
781/261                                          811/271
AAA TTT AAT GAG GAG AAG CTT TTA GAG CTT TTT AAT AAA TTA GAA TTC TTT AGT TTA ATT
 K   F   N   E   E   K   L   L   E   L   F   N   K   L   E   F   F   S   L   I
841/281                                          871/291
GAT AAC ATA AAG AAA GAA AGT AGC ATA GAG ATT GTA GAT AAT CAT AAA GTT GAA AAA TGG
 D   N   I   K   K   E   S   S   I   E   I   V   D   N   H   K   V   E   K   W
901/301                                          931/311
TCA AAA GTA GAT ATA AAA GAA TTA GTA ACT TTG TTG CAA GAT AAC AGA AAT ATT GCT TTT
 S   K   V   D   I   K   E   L   V   T   L   L   Q   D   N   R   N   I   A   F
961/321                                          991/331
TAC CCG TTA ATT TAT GAA GGG GAA ATA AAA AAA ATA GCC TTT TCT TTT GGA AAG GAT ACG
 Y   P   L   I   Y   E   G   E   I   K   K   I   A   F   S   F   G   K   D   T
1021/341                                         1051/351
GTT TAT ATT GAC GTT TTC CAA ACA GAA GAT TTA AAG GAG ATT TTT GAA AAA GAA GAT TTT
 V   Y   I   D   V   F   Q   T   E   D   L   K   E   I   F   E   K   E   D   F
1081/361                                         1111/371
GAA TTT ACA ACC CAT GAA ATA AAG GAT TTT TTA GTG AGG CTT TCT TAT AAA GGA ATA GAG
 E   F   T   T   H   E   I   K   D   F   L   V   R   L   S   Y   K   G   I   E
1141/381                                         1171/391
TGT AAA AGC AAG TAC ATA GAT ACT GCT GTA ATG GCT TAT CTT CTG AAT CCT TCT GAG TCT
 C   K   S   K   Y   I   D   T   A   V   M   A   Y   L   L   N   P   S   E   S
1201/401                                         1231/411
AAC TAT GAC TTA GAC CGT GTG CTA AAA AAA TAT TTA AAG GTA GAT GTG CCT TCT TAT GAA
 N   Y   D   L   D   R   V   L   K   K   Y   L   K   V   D   V   P   S   Y   E
1261/421                                         1291/431
GGA ATA TTT GGC AAA GGT AGG GAT AAA AAG AAA ATT GAA GAG ATT GAC GAA AAC ATA CTT
 G   I   F   G   K   G   R   D   K   K   K   I   E   E   I   D   E   N   I   L
1321/441                                         1351/451
GCT GAT TAT ATT TGC AGT AGA TGT GTG TAT CTA TTT GAT TTA AAA GAA AAG CTG ATG AAT
 A   D   Y   I   C   S   R   C   V   Y   L   F   D   L   K   E   K   L   M   N
1381/461                                         1411/471
TTT ATT GAA GAG ATG GAT ATG AAA AAA CTT CTA TTA GAA ATA GAA ATG CCT CTT GTA GAA
 F   I   E   E   M   D   M   K   K   L   L   L   E   I   E   M   P   L   V   E
```

*FIG. 2B*

```
1441/481                          1471/491
GTT TTA AAA TCA ATG GAG GTA AGT GGT TTT ACA TTG GAT AAA GAA GTT CTA AAA GAG CTT
 V   L   K   S   M   E   V   S   G   F   T   L   D   K   E   V   L   K   E   L
1501/501                          1531/511
TCA CAA AAG ATA GAT GAT AGA ATA GGA GAA ATA CTA GAT AAA ATT TAT AAA GAG GCA GGA
 S   Q   K   I   D   D   R   I   G   E   I   L   D   K   I   Y   K   E   A   G
1561/521                          1591/531
TAT CAA TTT AAT GTA AAT TCA CCT AAG CAA TTA AGT GAA TTT TTG TTT GAA AAG TTA AAC
 Y   Q   F   N   V   N   S   P   K   Q   L   S   E   F   L   F   E   K   L   N
1621/541                          1651/551
TTA CCA GTA ATA AAG AAA ACA AAA ACA GGA TAC TCT ACG GAT TCT GAA GTT TTG GAA CAA
 L   P   V   I   K   K   T   K   T   G   Y   S   T   D   S   E   V   L   E   Q
1681/561                          1711/571
TTG GTT CCT TAT AAT GAT ATT GTC AGC GAT ATA ATA GAG TAT CGG CAA CTT ACA AAA CTT
 L   V   P   Y   N   D   I   V   S   D   I   I   E   Y   R   Q   L   T   K   L
1741/581                          1771/591
AAA TCT ACT TAT ATA GAT GGA TTT TTG CCT CTT ATG GAT GAA AAC AAT AGA GTA CAT TCT
 K   S   T   Y   I   D   G   F   L   P   L   M   D   E   N   N   R   V   H   S
1801/601                          1831/611
AAT TTT AAA CAA ATG GTT ACT GCT ACA GGT AGA ATA AGC AGC ACC GAG CCA AAT CTA CAA
 N   F   K   Q   M   V   T   A   T   G   R   I   S   S   T   E   P   N   L   Q
1861/621                          1891/631
AAT ATA CCT ATA AGA GAA GAG TTT GGC AGA CAA ATT AGA AGG GCT TTT ATT CCG AGG AGT
 N   I   P   I   R   E   E   F   G   R   Q   I   R   R   A   F   I   P   R   S
1921/641                          1951/651
AGA GAT GGA TAT ATT GTT TCA GCA GAT TAT TCT CAG ATT GAA CTG AGG GTT TTA GCA CAT
 R   D   G   Y   I   V   S   A   D   Y   S   Q   I   E   L   R   V   L   A   H
1981/661                          2011/671
GTT TCG GGA GAT GAA AAG CTA ATA GAA TCT TTT ATG AAT AAT GAA GAT ATA CAT TTA AGG
 V   S   G   D   E   K   L   I   E   S   F   M   N   N   E   D   I   H   L   R
2041/681                          2071/691
ACA GCT TCG GAG GTT TTT AAA GTT CCT ATG GAA AAA GTT ACA CCG GAG ATG AGA AGA GCA
 T   A   S   E   V   F   K   V   P   M   E   K   V   T   P   E   M   R   R   A
2101/701                          2131/711
GCA AAA GCC GTA AAT TTT GGC ATA ATA TAT GGC ATA AGC GAT TAT GGG CTT TCT CGA GAC
 A   K   A   V   N   F   G   I   I   Y   G   I   S   D   Y   G   L   S   R   D
2161/721                          2191/731
```

*FIG. 2C*

```
CTT AAA ATA TCA AGA AAA GAA GCA AAA GAG TAC ATA AAT AAT TAT TTT GAA AGA TAT AAA
 L   K   I   S   R   K   E   A   K   E   Y   I   N   N   Y   F   E   R   Y   K
2221/741                                    2251/751

GGA GTA AAA GAT TAT ATT GAA AAA ATA GTA CGA TTT GCA AAA GAA AAT GGC TAT GTG ACT
 G   V   K   D   Y   I   E   K   I   V   R   F   A   K   E   N   G   Y   V   T
2281/761                                    2311/771

ACA ATA ATG AAC AGA AGG AGA TAT ATT CCT GAA ATA AAC TCA AGA AAT TTT ACT CAA AGA
 T   I   M   N   R   R   R   Y   I   P   E   I   N   S   R   N   F   T   Q   R
2341/781                                    2371/791

TCG CAG GCC GAA AGG TTA GCA ATG AAT GCT CCG ATA CAG GGA AGT GCG GCT GAT ATA ATA
 S   Q   A   E   R   L   A   M   N   A   P   I   Q   G   S   A   A   D   I   I
2401/801                                    2431/811

AAA ATG GCA ATG GTT AAG GTA TAC AAC GAT TTA AAA AAA TTA AAG CTT AAG TCT AAG CTT
 K   M   A   M   V   K   V   Y   N   D   L   K   K   L   K   L   K   S   K   L
2461/821                                    2491/831

ATA TTG CAA GTT CAT GAC GAG CTT GTA GTG GAT ACT TAT AAG GAT GAA GTA GAT ATC ATA
 I   L   Q   V   H   D   E   L   V   V   D   T   Y   K   D   E   V   D   I   I
2521/841                                    2551/851

AAA AAG ATA CTT AAA GAA AAT ATG GAA AAT GTA GTG CAA TTA AAA GTT CCT CTG GTT GTT
 K   K   I   L   K   E   N   M   E   N   V   V   Q   L   K   V   P   L   V   V
2581/861                                    2611/871

GAA ATT GGC GTA GGG CCT AAT TGG TTT TTG GCC AAG TGA
 E   I   G   V   G   P   N   W   F   L   A   K   *
```

*FIG. 2D*

MKLLELFNKLEFFSLIDNIKKESSIEIVDNHKVEKWSKVDIKELVTLLQDNRNIAFYPLIYEGEIK
KIAFSFGKDTVYIDVFQTEDLKEIFEKEDFEFTTHEIKDFLVRLSYKGIECKSKYIDT
AVMAYLL
NPSESNYDLDRVLKKYLKVDVPSYEGIFGKGRDKKKIEEIDENILADYICSRCVYLFDLKEKL
MNFIEEMDMKKLLLEIEMPLVEVLKSMEVSGFTLDKEVLKELSQKIDDRIGEILDKIYKEAGY
QFNVNSPKQLSEFLFEKLNLPVIKKTKTGYSTDSEVLEQLVPYNDIVSDIIEYRQLTKLKSTYID
GFLPLMDENNRVHSNFKQMVTATGRISSSEANLQNIPIREEFGRQIRRAFIPRSRDGYIVSADY
SQIELRVLAHVSGDEKLIESFMNNEDIHLRTASEVFKVPMEKVTPEMRRAAKAVNFGIIYGISD
YGLSRDLKISRKEAKEYINNYFERYKGVKDYIEKIVRFAKENGYVTTIMNRRRYIPEINSRNFT
QRSQAERLAMNAPIQGSAADIIKMAMVKVYNDLKKLKLKSKLILQVHDELVVDTYKDEVDII
KKILKENMENVVQLKVPLVVEIGVGPNWFLAK*

*FIG. 3*

```
1/1                                          31/11
ATG AAA GTT GAA AAA TGG TCT AAA GTA GAC ATC AAA GAA TTA GTA ACT TTG TTG CAA GAT
 M   K   V   E   K   W   S   K   V   D   I   K   E   L   V   T   L   L   Q   D
61/21                                        91/31
AAC AGA AAT ATT GCT TTT TAC CCG TTA ATT TAT GAA GGG GAA ATA AAA AAA ATA GCC TTT
 N   R   N   I   A   F   Y   P   L   I   Y   E   G   E   I   K   K   I   A   F
121/41                                       151/51
TCT TTT GGA AAG GAT ACG GTT TAT ATT GAC GTT TTC CAA ACA GAA GAT TTA AAG GAG ATT
 S   F   G   K   D   T   V   Y   I   D   V   F   Q   T   E   D   L   K   E   I
181/61                                       211/71
TTT GAA AAA GAA GAT TTT GAA TTT ACA ACC CAT GAA ATA AAG GAT TTT TTA GTG AGG CTT
 F   E   K   E   D   F   E   F   T   T   H   E   I   K   D   F   L   V   R   L
241/81                                       271/91
TCT TAT AAA GGA ATA GAG TGT AAA AGC AAG TAC ATA GAT ACT GCT GTA ATG GCT TAT CTT
 S   Y   K   G   I   E   C   K   S   K   Y   I   D   T   A   V   M   A   Y   L
301/101                                      331/111
CTG AAT CCT TCT GAG TCT AAC TAT GAC TTA GAC CGT GTG CTA AAA AAA TAT TTA AAG GTA
 L   N   P   S   E   S   N   Y   D   L   D   R   V   L   K   K   Y   L   K   V
361/121                                      391/131
GAT GTG CCT TCT TAT GAA GGA ATA TTT GGC AAA GGT AGG GAT AAA AAG AAA ATT GAA GAG
 D   V   P   S   Y   E   G   I   F   G   K   G   R   D   K   K   K   I   E   E
421/141                                      451/151
ATT GAC GAA AAC ATA CTT GCT GAT TAT ATT TGC AGT AGA TGT GTG TAT CTA TTT GAT TTA
 I   D   E   N   I   L   A   D   Y   I   C   S   R   C   V   Y   L   F   D   L
481/161                                      511/171
AAA GAA AAG CTG ATG AAT TTT ATT GAA GAG ATG GAT ATG AAA AAA CTT CTA TTA GAA ATA
 K   E   K   L   M   N   F   I   E   E   M   D   M   K   K   L   L   L   E   I
541/181                                      571/191
GAA ATG CCT CTT GTA GAA GTT TTA AAA TCA ATG GAG GTA AGT GGT TTT ACA TTG GAT AAA
 E   M   P   L   V   E   V   L   K   S   M   E   V   S   G   F   T   L   D   K
601/201                                      631/211
GAA GTT CTA AAA GAG CTT TCA CAA AAG ATA GAT GAT AGA ATA GGA GAA ATA CTA GAT AAA
 E   V   L   K   E   L   S   Q   K   I   D   D   R   I   G   E   I   L   D   K
661/221                                      691/231
ATT TAT AAA GAG GCA GGA TAT CAA TTT AAT GTA AAT TCA CCT AAG CAA TTA AGT GAA TTT
```

*FIG. 4A*

```
            I   Y   K   E   A   G   Y   Q   F   N   V   N   S   P   K   Q   L   S   E   F
721/241                                         751/251
TTG TTT GAA AAG TTA AAC TTA CCA GTA ATA AAG AAA ACA AAA ACA GGA TAC TCT ACG GAT
 L   F   E   K   L   N   L   P   V   I   K   K   T   K   T   G   Y   S   T   D
781/261                                         811/271
TCT GAA GTT TTG GAA CAA TTG GTT CCT TAT AAT GAT ATT GTC AGC GAT ATA ATA GAG TAT
 S   E   V   L   E   Q   L   V   P   Y   N   D   I   V   S   D   I   I   E   Y
841/281                                         871/291
CGG CAA CTT ACA AAA CTT AAA TCT ACT TAT ATA GAT GGA TTT TTG CCT CTT ATG GAT GAA
 R   Q   L   T   K   L   K   S   T   Y   I   D   G   F   L   P   L   M   D   E
901/301                                         931/311
AAC AAT AGA GTA CAT TCT AAT TTT AAA CAA ATG GTT ACT GCT ACA GGT AGA ATA AGC AGC
 N   N   R   V   H   S   N   F   K   Q   M   V   T   A   T   G   R   I   S   S
961/321                                         991/331
AGC GAG GCA AAT CTA CAA AAT ATA CCT ATA AGA GAA GAG TTT GGC AGA CAA ATT AGA AGG
 S   E   A   N   L   Q   N   I   P   I   R   E   E   F   G   R   Q   I   R   R
1021/341                                        1051/351
GCT TTT ATT CCG AGG AGT AGA GAT GGA TAT ATT GTT TCA GCA GAT TAT TCT CAG ATT GAA
 A   F   I   P   R   S   R   D   G   Y   I   V   S   A   D   Y   S   Q   I   E
1081/361                                        1111/371
CTG AGG GTT TTA GCA CAT GTT TCG GGA GAT GAA AAG CTA ATA GAA TCT TTT ATG AAT AAT
 L   R   V   L   A   H   V   S   G   D   E   K   L   I   E   S   F   M   N   N
1141/381                                        1171/391
GAA GAT ATA CAT TTA AGG ACA GCT TCG GAG GTT TTT AAA GTT CCT ATG GAA AAA GTT ACA
 E   D   I   H   L   R   T   A   S   E   V   F   K   V   P   M   E   K   V   T
1201/401                                        1231/411
CCG GAG ATG AGA AGA GCA GCA AAA GCC GTA AAT TAT GGC ATA ATA TAT GGC ATA AGC GAT
 P   E   M   R   R   A   A   K   A   V   N   Y   G   I   I   Y   G   I   S   D
1261/421                                        1291/431
TAT GGG CTT TCT CGA GAC CTT AAA ATA TCA AGA AAA GAA GCA AAA GAG TAC ATA AAT AAT
 Y   G   L   S   R   D   L   K   I   S   R   K   E   A   K   E   Y   I   N   N
1321/441                                        1351/451
TAT TTT GAA AGA TAT AAA GGA GTA AAA GAT TAT ATT GAA AAA ATA GTA CGA TTT GCA AAA
 Y   F   E   R   Y   K   G   V   K   D   Y   I   E   K   I   V   R   F   A   K
1381/461                                        1411/471
GAA AAT GGC TAT GTG ACT ACA ATA ATG AAC AGA AGG AGA TAT ATT CCT GAA ATA AAC TCA
 E   N   G   Y   V   T   T   I   M   N   R   R   R   Y   I   P   E   I   N   S
1441/481                                        1471/491
```

*FIG. 4B*

```
AGA AAT TTT ACT CAA AGA TCG CAG GCC GAA AGG TTA GCA ATG AAT GCT CCG ATA CAG GGA
 R   N   F   T   Q   R   S   Q   A   E   R   L   A   M   N   A   P   I   Q   G
1501/501                                    1531/511
AGT GCG GCT GAT ATA ATA AAA ATG GCA ATG GTT AAG GTA TAC AAC GAT TTA AAA AAA TTA
 S   A   A   D   I   I   K   M   A   M   V   K   V   Y   N   D   L   K   K   L
1561/521                                    1591/531
AAG CTT AAG TCT AAG CTT ATA TTG CAA GTT CAT GAC GAG CTT GTA GTG GAT ACT TAT AAG
 K   L   K   S   K   L   I   L   Q   V   H   D   E   L   V   V   D   T   Y   K
1621/541                                    1651/551
GAT GAA GTA GAT ATC ATA AAA AAG ATA CTT AAA GAA AAT ATG GAA AAT GTA GTG CAA TTA
 D   E   V   D   I   I   K   K   I   L   K   E   N   M   E   N   V   V   Q   L
1681/561                                    1711/571
AAA GTT CCT CTG GTT GTT GAA ATT GGC GTA GGG CCT AAT TGG TTT TTG GCC AAG TGA
 K   V   P   L   V   V   E   I   G   V   G   P   N   W   F   L   A   K   *
```

*FIG. 4C*

```
ATGGCTTATAAATTTTTAATCATTGATGGTAGTAGCCTCATGTACAGAG
CCTATTATGCCTTGCCCATGCTTACTACAAGTGAGGGATTGCCTACAAATGCTCTGTA
TGGTTTTACTATGATGCTTATA
AAACTTATCGAGGAGGAAAAACCTGATTACATAGCTATTGCTTTTGACAAAAAAGCT
CCTACTTTTAGACACAAAGAATA
TCAAGACTACAAAGCTACAAGACAAGCTATGCCTGAAGAACTTGCTGAACAAGTAGA
CTATTTGAAAGAAATTATAGATG
GCTTTAATATAAAGACATTAGAATTAGAAGGTTATGAAGCTGATGACATTATAGGGA
CTATTTCAAAGCTGGCAGAGGAA
AAAGGAATGGAAGTGCTTGTAGTTACAGGAGACAGAGATGCTCTTCAATTAGTTTCA
GATAAAGTGAAGATAAAAATTTC
TAAAAAGGGTATTACTCAGATGGAAGAGTTTGACGAAAAGGCTATTTTAGAAAGGTA
TGGAATAACTCCTCAGCAGTTTA
TAGATTTAAAAGGGCTTATGGGAGATAAATCTGATAATATCCCTGGAGTACCTAATAT
AGGGGAAAAAACTGCGATTAAG
CTATTAAAGGATTTTGGAACAATTGAAAATTTAATCCAAAATCTTTCTCAGCTTAAAG
GTAAAATAAAAGAAAATATAGA
AAACAATAAAGAGTTAGCTATAATGAGTAAGAGGCTTGCTACTATAAAAAGAGACAT
TCCCATTGAGATAGATTTTGAGG
AGTATAAAGTAAAAAAATTTAATGAGGAGAAGCTTTTAGAGCTTTTTAATAAATTAGA
ATTCTTTAGTTTAATTGATAAC
ATAAAGAAAGAAAGTAGCATAGAGATTGTAGATAATCATAAAGTTGAAAAATGGTCA
AAAGTAGATATAAAAGAATTAGT
AACTTTGTTGCAAGATAACAGAAATATTGCTTTTTACCCGTTAATTTATGAAGGGGAA
ATAAAAAAAATAGCCTTTTCTT
```

*FIG. 7A*

TTGGAAAGGATACGGTTTATATTGACGTTTTCCAAACAGAAGATTTAAAGGAGATTTT
TGAAAAAGAAGATTTTGAATTT
ACAACCCATGAAATAAAGGATTTTTTAGTGAGGCTTTCTTATAAAGGAATAGAGTGTA
AAAGCAAGTACATAGATACTGC
TGTAATGGCTTATCTTCTGAATCCTTCTGAGTCTAACTATGACTTAGACCGTGTGCTAA
AAAAATATTTAAAGGTAGATG
TGCCTTCTTATGAAGGAATATTTGGCAAAGGTAGGGATAAAAAGAAAATTGAAGAGA
TTGACGAAAACATACTTGCTGAT
TATATTTGCAGTAGATGTGTGTATCTATTTGATTTAAAAGAAAAGCTGATGAATTTTAT
TGAAGAGATGGATATGAAAAA
ACTTCTATTAGAAATAGAAATGCCTCTTGTAGAAGTTTTAAAATCAATGGAGGTAAGT
GGTTTTACATTGGATAAAGAAG
TTCTAAAAGAGCTTTCACAAAAGATAGATGATAGAATAGGAGAAATACTAGATAAAA
TTTATAAAGAGGCAGGATATCAA
TTTAATGTAAATTCACCTAAGCAATTAAGTGAATTTTTGTTTGAAAAGTTAAACTTACC
AGTAATAAAGAAAACAAAAAC
AGGATACTCTACGGATTCTGAAGTTTTGGAACAATTGGTTCCTTATAATGATATTGTC
AGCGATATAATAGAGTATCGGC
AACTTACAAAACTTAAATCTACTTATATAGATGGATTTTTGCCTCTTATGGATGAAAA
CAATAGAGTACATTCTAATTTT
AAACAAATGGTTACTGCTACAGGTAGAATAAGCAGCACCGAGCCAAATCTACAAAAT
ATACCTATAAGAGAAGAGTTTGG
CAGACAAATTAGAAGGGCTTTTATTCCGAGGAGTAGAGATGGATATATTGTTTCAGCA
GATTATTCTCAGATTGAACTGA
GGGTTTTAGCACATGTTTCGGGAGATGAAAAGCTAATAGAATCTTTTATGAATAATGA

*FIG. 7B*

```
AGATATACATTTAAGGACAGCT
TCGGAGGTTTTTAAAGTTCCTATGGAAAAAGTTACACCGGAGATGAGAAGAGCAGCA
AAAGCCGTAAATTTTGGCATAAT
ATATGGCATAAGCGATTATGGGCTTTCTCGAGACCTTAAAATATCAAGAAAAGAAGC
AAAAGAGTACATAAATAATTATT
TTGAAAGATATAAAGGAGTAAAAGATTATATTGAAAAAATAGTACGATTTGCAAAAG
AAAATGGCTATGTGACTACAATA
ATGAACAGAAGGAGATATATTCCTGAAATAAACTCAAGAAATTTTACTCAAAGATCG
CAGGCCGAAAGGTTAGCAATGAA
TGCTCCGATACAGGGAAGTGCGGCTGATATAATAAAAATGGCAATGGTTAAGGTATA
CAACGATTTAAAAAAATTAAAGC
TTAAGTCTAAGCTTATATTGCAAGTTCATGACGAGCTTGTAGTGGATACTTATAAGGA
TGAAGTAGATATCATAAAAAAG
ATACTTAAAGAAAATATGGAAAATGTAGTGCAATTAAAAGTTCCTCTGGTTGTTGAAA
TTGGCGTAGGGCCTAATTGGTT
TTTGGCCAAGTGA
```

*FIG. 7C*

THERMOSTABLE DNA POLYMERASE FROM *THERMOANAEROBACTER THERMOHYDROSULFURICUS*

This application claims priority to Provisional Application, Mamone et al., U.S. Ser. No. 60/008,688 filed Dec. 15, 1995, entitled "Thermostable DNA Polymerase.

BACKGROUND OF THE INVENTION

The present invention relates to novel thermostable DNA polymerases obtainable from the thermophilic anaerobe *Thermoanaerobacter thermohydrosulfuricus*, to certain deletants and mutants of this enzyme, to genes and vectors encoding the wild type and mutant polymerases and their use in strand displacement activity, polymerase chain reaction, DNA sequencing and as reverse transcriptases.

The following is a discussion of the relevant art, none of which is admitted to be prior art to the appended claims.

DNA polymerases are a family of enzymes involved in DNA repair and replication. DNA polymerases have been isolated from *E. coli* (e.g. *E. coli* DNA polymerase I and the Klenow fragment thereof) and T4 DNA polymerase and more recently thermostable DNA polymerases have been isolated (e.g. from *T. aquaticus*, U.S. Pat. No. 4,889,818, and from *T. litoralis*). Thermostable DNA polymerases have been suggested (U.S. Pat. No. 4,683,195) for use in amplifying existing nucleic acid sequences in amounts that are large compared to that originally present. The polymerase chain reaction (PCR) and strand displacement amplification (SDA) are two methods of amplifying nucleic acid sequences.

PCR is based on the hybridization of oligonucleotide primers to specific sequences on opposite strands of the target DNA molecule, and subsequent extension of these primers with a DNA polymerase to generate two new strands of DNA which themselves can serve as a template for a further round of hybridization and extension. In PCR reactions the product of one cycle serves as the template for the next cycle such that at each repeat of the cycle the amount of the specific sequence present in the reaction doubles leading to an exponential amplification process.

PCR relies on a process of temperature cycling to promote the amplification reaction. This temperature cycling is necessary to separate the strands of DNA formed in one cycle of the reaction to allow hybridization of the oligonucleotides required to initiate the next cycle. DNA strand separation is usually achieved by melting the DNA at temperatures in the range 90°–100° C. followed by cooling to a lower temperature to allow oligonucleotide hybridization followed by extension or ligation, depending on the reaction process. This cycling process may be repeated 20–50 times, again depending on the process and the degree of amplification required.

Temperature cycling is normally achieved by the use of specialized equipment, commonly termed thermocyclers, which can operate by a wide variety of mechanical, electrical or hydraulic means, but serve a common purpose in heating and cooling a small container or a number of such containers in which the amplification reaction is performed.

In order for the amplification reactions to proceed with the desired efficiency and specificity it is necessary to perform the temperature cycling process within strictly defined and reproducible limits of temperature and time. Failure of the temperature cycling apparatus to achieve the required conditions will result in the partial or total failure of the amplification reaction. These strict requirements on time and temperature of cycling can impose severe restrictions if the handling of large numbers of reactions is required. If it is desired to perform several hundred or more reactions simultaneously use of conventional thermocyclers would be extremely expensive in terms of the capital investment required in equipment, and would in any case be prone to variations between individual thermocyclers. Alternative solutions for large scale use have been constructed based on fan assisted oven or multiple water baths, but such solutions are inevitably cumbersome in use and in any case still require the user to take the normal stringent steps to avoid evaporation which become extremely difficult to apply to a large number of cycles.

In reverse transcription/polymerase chain reaction (RT/PCR), a DNA primer is hybridized to a strand of the target RNA molecule, and subsequent extension of this primer with a reverse transcriptase generates a new strand of DNA which can serve as a template for PCR. Preparation of the DNA template is preferably carried out at an elevated temperature to avoid early termination of the reverse transcriptase reaction caused by RNA secondary structure. There is a lack of efficient reverse transcriptases that act at elevated temperatures, e.g. above 50° C.

SDA differs from PCR in being an isothermal amplification process, i.e. all reactions occur at the same temperature without the need for elevated temperature to melt DNA strands. This is made possible by adoption of a reaction scheme which uses the ability of certain DNA polymerases when extending along a DNA template strand to displace any DNA molecules already hybridized to the template. In SDA this strand displacement is used to separate the double stranded DNA produced during the reaction process and hence to maintain continuous amplification of the target DNA sequence (Walker, G. T., Little, M. C., Nadeau, J. G. and Shank D. D. (1992) *Proc. Natl. Acad. Sci. USA* 89:392–396). SDA is therefore in principle more suited to use with large numbers of samples than PCR as the isothermal process, which is performed at temperatures of 37° C. to 60° C., does not require stringent precautions to be taken to avoid evaporation and can be performed with simple temperature control equipment, for example in a standard laboratory incubator.

DNA polymerases, e.g. Sequenase, Klenow, Taq, etc, have also been extensively used in DNA sequencing, see for example U.S. Pat. No. 5,173,411.

SUMMARY OF THE INVENTION

The present invention provides a thermostable DNA polymerase from *Thermoanaerobacter thermohydrosulfuricus*. This enzyme is useful for procedures requiring stranddisplacing DNA synthesis such as SDA, for DNA sequencing and/or for reverse transcription. Included within the scope of the present invention are various mutants (deletion and substitution) that retain thermostability and the ability to replicate DNA with substantially the same efficiency as the native *Thermoanaerobacter thermohydrosulfuricus* polymerase.

In a first aspect, the present invention provides a purified DNA polymerase or fragment thereof having the DNA polymerase activity of *Thermoanaerobacter thermohydrosulfuricus* and having at least 80% amino acid homology, preferably at least 90% homology, to at least a contiguous 40 amino acid sequence shown in FIG. 2A–D (SEQ. ID. NO. 2). FIGS. 2A–D represents the translation of an open reading frame spanning nucleotides 1056–3674 of genomic DNA encoding a thermostable DNA polymerase from *Thermoa-* naerobacter thermohydrosulfuricus (FIGS. 1A–E) (SEQ. ID. NO. 1) potentially encoding the native polymerase.

When used herein, the term amino acid homology means the amino acid identity of the parent enzyme or conservative amino acid changes thereto.

The purified enzyme of the present invention has a molecular weight of approximately 90,000 daltons when measured on SDS-PAGE. It possesses a 5'-3' exonuclease activity. The temperature optimum of DNA synthesis is near 75° C. under assay conditions. The optimum magnesium ion and manganese ion concentrations for DNA synthesis are 1 mM and 0.5 mM respectively.

The term thermostable polymerase means an enzyme which is stable to heat (and heat resistant) and is suitable for use in SDA and/or sequencing at an elevated temperature, for example 70° C. The thermostable enzyme herein must satisfy a single criterion to be effective for the amplification reaction, i.e., the enzyme must not become irreversibly denatured (inactivated) when subjected to the elevated temperatures for the time necessary to effect amplification. Irreversible denaturation for purposes herein refers to permanent and complete loss of enzymatic activity. Preferably, the enzyme will not become irreversibly denatured at about 70° C. but may become denatured at higher temperatures. The thermostable enzyme herein preferably has an optimum temperature at which it functions that is higher than about 40° C., which is the temperature below which hybridization of primer to template is promoted, although, depending on (1) salt concentration and composition and (2) composition and length of primer, hybridization can occur at higher temperature (e.g., 45°–70° C.). The higher the temperature optimum for the enzyme, the greater the specificity and/or selectivity of the primer-directed extension process. However, enzymes that are active below 40° C., e.g., at 37° C., are also within the scope of this invention provided they are heat stable. Preferably, the optimum temperature ranges from about 50° to 80° C., more preferably 50°–70° C.

When used herein, the term a DNA polymerase or fragment thereof having the DNA polymerase activity of *Thermoanaerobacter thermohydrosulfuricus* means a DNA polymerase or fragment thereof (as hereinafter defined) which has the ability to replicate DNA with substantially the same efficiency as the enzyme encoded by the SEQ. ID. NO. 1. By substantially the same efficiency is meant at least 80% and preferably at least 90% of the efficiency of the enzyme encoded by SEQ. ID. NO. 1 to incorporate deoxynucleotides.

The invention also encompasses a stable enzyme composition which comprises a purified thermostable DNA polymerase from *Thermoanaerobacter thermohydrosulfuricus* in a buffer.

The DNA polymerases of the present invention are preferably in a purified form. By purified is meant that the DNA polymerase is isolated from a majority of host cell proteins normally associated with it; preferably the polymerase is at least 10% (w/w), e.g. at least 50% (w/w), of the protein of a preparation, even more preferably it is provided as a homogeneous preparation, e.g. homogeneous solution. Preferably the DNA polymerase is a single polypeptide on an SDS polyacrylamide gel.

Buffers around neutral pH (5-9) such as 5–100 mM Tris-HCl, phosphate or MES are suitable for use in the current invention.

The present invention also provides a gene encoding a polymerase of the present invention. FIGS. 1A–E represents nucleotides 1–5300 of a cloned genomic sequence encompassing the gene encoding the polymerase of the present invention (SEQ. ID. NO. 1). FIGS. 7A–C represents the DNA sequence of a full length native polymerase from *Thermoanaerobacter thermohydrosulfuricus* (SEQ. ID. NO. 23).

It has been found that the entire amino acid sequence of the polymerase is not required for enzymatic activity. Thus, for example, the exonuclease domain of the enzyme has been deleted to give an enzyme of molecular weight of approximately 64,000 daltons when measured on SDS-PAGE which retains enzyme activity and also has reverse transcriptase activity making it useful for making cDNA. This exonuclease-free enzyme is analogous to the Klenow fragment of *E. coli* DNA polymerase I. Thus, the present invention also provides fragments of the polymerase which retain the DNA polymerase activity of *Thermoanaerobacter thermohydrosulfuricus* but have one or more amino acids deleted, preferably from the amino-terminus, while still having at least 80% amino acid homology to at least a 40 contiguous amino acid sequence shown in FIGS. 2A–D (SEQ. ID. NO. 2).

In a further aspect, the present invention provides a thermostable DNA polymerase which corresponds to the DNA polymerase from *Thermoanaerobacter thermohydrosulfuricus* in which up to one third of the amino acid sequence at the amino-terminus has been deleted. In particular, fragments of *Thermoanaerobacter thermohydrosulfuricus* having N-terminal deletions to give 578 amino acids (See FIGS. 4A–C) (SEQ. ID. NO. 4) and 608 amino acids (See FIG. 3) (SEQ. ID. NO. 3) have been found to retain enzyme activity.

It is preferred that the 5'-3' exonuclease activity of the DNA polymerase is removed or reduced. This may be achieved by deleting the amino acid region of the enzyme responsible for this activity, e.g. by deleting up to one third of the amino acid sequence at the amino terminus, or by appropriate amino acid changes.

In addition to the N-terminal deletions and amino acid changes to remove the exonuclease activity, the enzyme may have conservative amino acid changes compared with the native enzyme which do not significantly influence thermostability or enzyme activity. Such changes include substitution of like charged amino acids for one another or amino acids with small side chains for other small side chains, e.g. ala for val. More drastic changes may be introduced at non-critical regions where little or no effect on polymerase activity is observed by such a change.

Joyce and Steitz, *Annu. Rev. Biochem*, 63:777–822, 1994, discuss various functions of DNA polymerases including the catalytic center, the binding site for the 3' terminus of the primer, and the dNTP binding site. In particular, it mentions mutations that affect the binding of dNTP in the ternary complex. European Patent Application 0655506A discloses that the presence of a polar, hydroxyl containing amino acid residue at a position near the binding site for the dNTP substrate is important for the polymerase being able to efficiently incorporate a dideoxynucleotide. Applicant has discovered that the modification of the dNTP binding site for the dNTP substrate in DNA polymerase obtainable from *Thermoanaerobacter thermohydrosulfuricus* by the inclusion of a polar, hydroxyl containing amino acid residue at a position near the binding site increases the efficiency of the polymerase to incorporate a dideoxynucleotide. Preferably the polar, hydroxyl containing amino acid is tyrosine. It has also been found that replacing the phenylalanine at the position corresponding to 706 of the native enzyme with tyrosine improves the incorporation of dideoxynucleotides when the enzyme is used for sequencing. In particular, a polymerase from *Thermoanaerobacter thermohydrosulfuricus* in which the exonuclease activity has been deleted e.g. by point mutation or deletion and which has the phenylalanine at the position corresponding to 706 of the native enzyme replaced by an amino acid which increases the efficiency of the enzyme to incorporate dideoxynucleotides at least 20 fold compared to the wild type enzyme, e.g. tyrosine, is a particularly preferred enzyme for use in sequencing. Preferably, this modified enzyme has from between 540 and 582 amino acids, for example 560 to 582 amino acids and preferably 578 amino acids.

The DNA polymerases of the present invention can be constructed using standard techniques familiar to those who practice the art. By way of example, in order to prepare a polymerase with the phenylalanine to tyrosine mutation, mutagenic PCR primers can be designed to incorporate the desired Phe to Tyr amino acid change (FY mutation in one primer). Deletion of the exonuclease function is carried out by PCR to remove the amino terminus, or standard techniques of site directed mutagenesis to generate point mutations.

Improved expression of the DNA polymerases of the present invention can be achieved by introducing silent codon changes (i.e., the amino acid encoded is not changed). Such changes can be introduced by the use of mutagenic PCR primers. Silent codon changes such as the following increase protein production in *E. coli:* substitution of the codon GAG for GAA;

substitution of the codon AGG, AGA, CGG or CGA for CGT or CGC;

substitution of the codon CTT, CTC, CTA, TTG or TTA for CTG;

substitution of the codon ATA for ATT or ATC;

substitution of the codon GGG or GGA for GGT or GGC.

Genes encoding the DNA polymerase from *Thermoanaerobacter thermohydrosulfuricus* polymerases in which up to one third of the amino acid sequence at the amino terminus has been deleted and such polymerases which incorporate the phenylalanine to tyrosine modification are also provided by the present invention.

In a yet further aspect, the present invention provides a host cell comprising a vector containing the gene encoding the DNA polymerase activity of the present invention, e.g., encoding an amino acid sequence corresponding to native *Thermoanaerobacter thermohydrosulfuricus* or differentiated from this in that it lacks up to one third of the N-terminal amino acids and optionally has phenylalanine at position 706 replaced by tyrosine.

The DNA polymerases of the present invention are suitably used in SDA, preferably in combination with a thermostable restriction enzyme. Accordingly, the present invention provides a composition which comprises a DNA polymerase of the present invention in combination with a thermostable restriction enzyme, for example BsoBI from *Bacillus stearothermophilus*. The invention also features a kit or solution for SDA comprising a DNA polymerase of the present invention in combination and a thermostable restriction enzyme.

The polymerases of the present invention are also useful in methods for generating and amplifying a nucleic acid fragment via a strand displacement amplification (SDA) mechanism. The method generally comprises:

a) specifically hybridizing a first primer 5' to a target nucleic acid sequence, the first primer containing a restriction enzyme recognition sequence 5' to a target binding region;

b) extending the 3' ends of the hybridized material using a DNA polymerase of the present invention, preferably one in which the exonuclease activity has been removed, in the presence of three dNTPs and one dNTP$\propto$ S;

c) nicking at the hemiphosphorothioate recognition site with a restriction enzyme, preferably;

d) extending the 3' end at the nick using a DNA polymerase of the present invention, displacing the downstream complement of the target strand; and e) repeating steps (c) and (d).

This SDA method proceeds at a linear amplification rate if one primer is used as above. However, if two primers are used which hybridize to each strand of a double-stranded DNA fragment, then the method proceeds exponentially (Walker, G. T., Little, M. C., Nadeau, J. G. and Shank D. D. (1992) *Proc. Natl. Acad. Sci. USA* 89:392–396).

The present invention also provides a method for determining the nucleotide base sequence of a DNA molecule. The method includes providing a DNA molecule, annealing with a primer molecule able to hybridize to the DNA molecule; and incubating the annealed molecules in a vessel containing at least one, and preferably four deoxynucleotide triphosphate, and a DNA polymerase of the present invention preferably one containing the phenylalanine to tyrosine mutation. Also provided is at least one DNA synthesis terminating agent which terminates DNA synthesis at a specific nucleotide base. The method further includes separating the DNA products of the incubating reaction according to size, whereby at least a part of the nucleotide base sequence of the DNA molecule can be determined.

In preferred embodiments, the sequencing is performed at a temperature between 40° and 75° C.

In other preferred embodiments, the DNA polymerase has less than 1000, 250, 100, 50, 10 or even 2 units of exonuclease activity per mg of polymerase (measured by standard procedure, see below) and is able to utilize primers having only 4, 6 or 10 bases; and the concentration of all four deoxynucleoside triphosphates at the start of the incubating step is sufficient to allow DNA synthesis to continue until terminated by the agent, e.g. a ddNTP.

Preferably, more than 2, 5, 10 or even 100 fold excess of a dNTP is provided to the corresponding ddNTP.

In a related aspect, the invention features a kit or solution for DNA sequencing including a DNA polymerase of the present invention and a reagent necessary for the sequencing such as dITP, deaza dGTP, a chain terminating agent such as a ddNTP, and optionally a pyrophosphatase.

The DNA polymerases of the present invention containing the phenylalanine to tyrosine mutation are suitably used in sequencing, preferably in combination with a pyrophosphatase. Accordingly, the present invention provides a composition which comprises a DNA polymerase of the present invention containing the phyenylalanine to tyrosine mutation in combination with a pyrophosphatase, preferably a thermostable pyrophosphatase from *Thermoplasma acidophilum*.

In another related aspect, the invention features a method for sequencing a strand of DNA essentially as described above with one or more (preferably 2, 3 or 4) deoxyribonucleoside triphosphates, a DNA polymerase of the present invention, and a first chain terminating agent. The DNA polymerase causes the primer to be elongated to form a first series of first DNA products differing in the length of the elongated primer, each first DNA product having a chain terminating agent at its elongated end, and the number of molecules of each first DNA products being approximately the same for substantially all DNA products differing in length by no more than 20 bases. The method also features providing a second chain terminating agent in the hybridized mixture at a concentration different from the first chain terminating agent, wherein the DNA polymerase causes production of a second series of second DNA products differing in length of the elongated primer, with each second DNA product having the second chain terminating agent at its elongated end. The number of molecules of each second DNA product is approximately the same for substantially all second DNA products differing in length from each other by from 1 to 20 bases, and is distinctly different from the number of molecules of all the first DNA products having a length differing by no more than 20 bases from that of said second DNA products.

In preferred embodiments, three or four such chain terminating agents can be used to make different products and the sequence reaction is provided with a magnesium ion, or even a manganese or iron ion (e.g. at a concentration between 0.05 and 100 mM, preferably between 1 and 10 mM); and the DNA products are separated according to molecular weight in four or less lanes of a gel.

In another related aspect, the invention features a method for sequencing a nucleic acid by combining an oligonucleotide primer, a nucleic acid to be sequenced, between one and four deoxyribonucleoside triphosphates, a DNA polymerase of the present invention, and at least two chain terminating agents in different amounts, under conditions favoring extension of the oligonucleotide primer to form nucleic acid fragments complementary to the nucleic acid to be sequenced. The method further includes separating the nucleic acid fragments by size and determining the nucleic acid sequence. The agents are differentiated from each other by intensity of a label in the primer extension products.

In a further aspect, the present invention provides a method for preparing complementary DNA by combining an oligonucleotide primer, a sample of RNA, a DNA polymerase of the present invention, and between one and four deoxyribonucleoside phosphates, under conditions favoring preparation of the complementary DNA.

The DNA polymerases of the present invention which act as reverse transcriptases lack appreciable, and preferably have no RNaseH activity and, as such, are useful in RT/PCR, the generation of hybridization probes and RNA sequencing. In a yet further aspect, the present invention provides a purified thermostable reverse transcriptase having a reverse transcriptase activity of greater than 1000 units per milligram. Preferably, the reverse transcriptase lacks RNaseH activity; the reverse transcriptase is from *Thermoanaerobacter thermohydrosulfuricus*; the reverse transcriptase has an N-terminal deletion or amino acid changes that remove the exonuclease function. In a further aspect, the invention features a method for reverse transcription/polymerase chain reaction (RT/PCR) which utilizes a DNA polymerase of the present invention and a DNA polymerase suitable for PCR in the same reaction vessel. Preferably, the DNA polymerase of the present invention is from *Thermoanaerobacter thermohydrosulfuricus*, the polymerase has one or more amino acids deleted from the amino terminus or amino acid changes to remove the exonuclease activity, the DNA polymerase suitable for PCR is Taq DNA polymerase. In another aspect, the present invention features a kit or solution for RT/PCR comprising a DNA polymerase of the present invention and a DNA polymerase suitable for PCR. Preferably, the DNA polymerase of the present invention is from *Thermoanaerobacter thermohydrosulfuricus*, the polymerase has one or more amino acids deleted from the amino terminus or amino acid changes to remove the exonuclease function, the DNA polymerase suitable for PCR is Taq DNA polymerase.

Other features and advantages of the invention will be apparent from the following description of the preferred embodiments thereof, and from the claims.

DESCRIPTION OF THE PREFERRED EMBODIMENTS

The drawings will first be briefly described.
Drawings

FIGS. 1A–E is the DNA sequence for 5300 bp of genomic DNA flanking and encoding the full length DNA polymerase from *Thermoanaerobacter thermohydrosulfuricus* (SEQ. ID. NO. 1).

FIGS. 2A–D is a contiguous open reading frame capable of encoding the full length polymerase from *Thermoanaerobacter thermohydrosulfuricus* (SEQ. ID. NO. 2). Translation is of an open reading frame spanning nucleotides 1056–3674 of genomic DNA in FIGS. 1A–E, potentially encoding native polymerase.

FIG. 3 is the contiguous open reading frame of nucleotides 796–2616, amino acids 266–872 plus an initiator methionine at the amino terminus, the exo⁻ mutant of the enzyme containing 608 amino acids (SEQ. ID. NO. 3).

FIGS. 4A–C is the contiguous open reading frame of the F412Y mutation of the exo-mutant polymerase, containing 578 amino acids with. (SEQ. ID. NO. 4). At amino acid 412 there is a tyrosine replacing phenylalanine.

Figure 5:
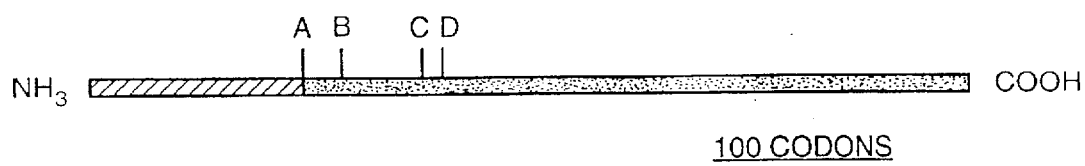

FIG. 5 is a schematic of cloned polymerases. Letters A–D represent start sites of the various constructs shown in the table in Example 2.

Figure 6:
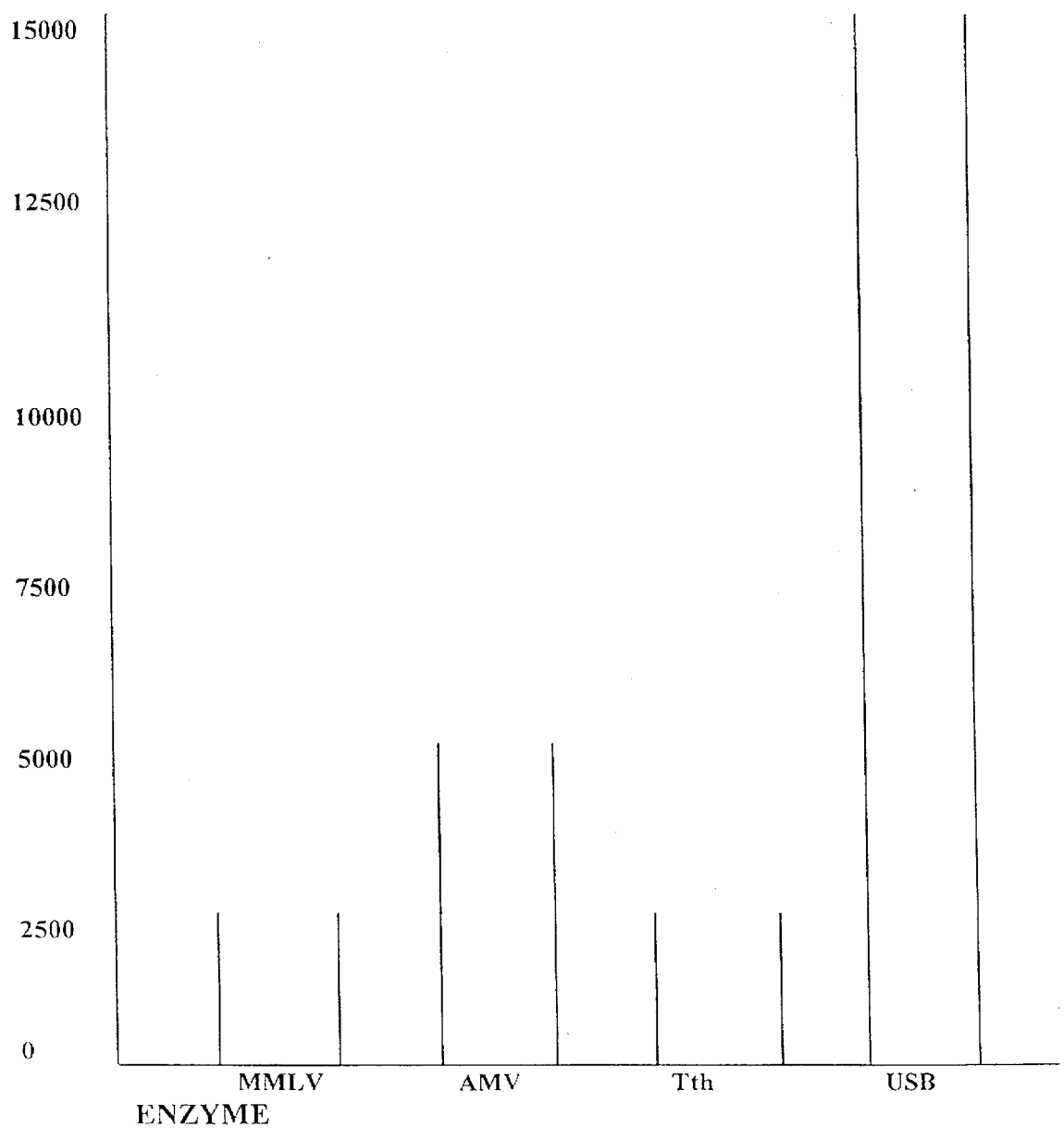

FIG. 6 is a graphical representation comparing relative RT activity of the exo- mutant enzyme and other enzymes that have reverse transcription activity. The x-axis indicates the polymerase (MMLV, AMV, Tth, USB). The y-axis represents reverse transcriptase activity in cpm.

FIGS. 7A–C is the DNA sequence encoding a full length native polymerase from *Thermoanaerobacter thermohydrosulfuricus* (SEQ. ID. NO. 23).

EXAMPLES

The following examples serve to illustrate the DNA polymerases of the present invention.

Example 1

General Methods Used During Purification and Characterization

Assay of DNA Polymerase Activity

DNA polymerase activity was assayed by measuring the amount of incorporation of a radiolabelled deoxynucleotide into acid percipitable material using activated salmon sperm DNA as a template (Richardson, C. C. (1966) DNA polymerase from *Escherichia coli*, pp. 263–276 In G. L. Cantoni and D. R. Davies (ed.), Procedures in nucleic acid research. Harper and Row, New York). A unit of DNA polymerase is the amount of enzyme that catalyzes incorporation of 10 nmoles of deoxynucleotide triphosphate into acid-precipitable material in 30 minutes at 70° C. An assay consists of 2–10 µl of protein solution containing DNA polymerase being incubated with 50 µl of assay mix (20 mM Tris HCl pH 8.5 @ room temperature, 200 µM each deoxynucleotide triphosphate, 10 mM KCl, 5 mM MgCl$_2$, 0.2 mg/ml activated salmon sperm DNA, 1 µCi 3000 Ci/mmole

[α-³³P]dATP) at 70° C. for 10 minutes. The reaction is stopped by adding the contents of the assay to a tube containing 1 ml each of carrier (50 µg/ml fish sperm DNA, 2 mM EDTA) and precipitant (20% (w/v) trichloroacetic acid, 2% (w/v) sodium pyrophosphate). After incubation on ice for at least 5 minutes, the solution is filtered through a glass fiber filter (e.g. GF/B, Whatman), washed with several milliliters ice-cold wash solution (1N hydrochloric acid, 100 mM sodium pyrophosphate), placed in a counting vial with aqueous liquid scintillation cocktail (e.g. Biosafe II, Research Products International Corp.) and counted in a liquid scintillation counter. DNA polymerase activity of the test solution is calculated from the measured specific activity of the assay mix. Only activity values measured to be within the linear range of 0.01 to 0.2 units per assay reaction were accepted as significant.

Measurement of Protein Concentration

Solution protein concentrations are measured spectrophotometrically by determining the absorbance of the test solution at a wavelength of 205 nm ($A_{205}$) (Scopes, R. K. (1994) pp. 46–48 Protein Purification. Springer-Verlag, New York). The extinction coefficient of polypeptides is taken as $E_{205}$(1 mg/ml)=31.

Assay of Exonuclease Activity

Exonuclease activity was measured as described (Kong, H., Kucera, R. B. and Jack, W. E. (1993) *J. Biol. Chem.* 268, 1965–1975) using, as substrate, HindIII digested phage λ DNA labeled with ³H by the action of CpG methylase or a 500 bp PCR product generated from pBR322 labeled with ³H by incorporation of tritiated TTP. Exonuclease assays were performed in the same buffer (20 mM Tris.HCl pH 8.5 @ room temperature, 10 mM KCl, 5 mM $MgCl_2$) and at the same temperature (70° C.) as polymerase assays.

Assay for Directionality of Exonuclease

The directionality of the associated exonuclease activity was determined by monitoring the time-dependent release of radioactivity from a DNA substrate differentially labeled on the 5' and 3' ends as described (Kong et al., supra).

Assay for Strand Displacement Activity

An extension assay has been developed to evaluate polymerases for their utility in the SDA (strand displacement amplification) reaction (Becton-Dickinson). This extension reaction tests the ability of the polymerase to displace a downstream strand and its ability to initiate extension at a nick site. This displacement and initiation at a nick is staged by annealing two primers labeled at their 5' ends immediately adjacent to each other. If the polymerase has strand displacement activity and is able to initiate at a nick, both primers are extended and two extension products can be visualized. If the polymerase cannot initiate at a nick (that is, it has a preference for initiation at a gap) or it lacks displacement activity then only the downstream primer is extended and only one product is detected.

Using the plasmid pBR322 as the target, two primers pBR1 and pBR2 were synthesized that anneal immediately adjacent to each other on the plasmid. Primer PBR1 is the upstream primer and corresponds to bases 3661 to 3690 in pBR322 (GGTTCCCAACGATCAAGGCGAGTTACATGA) (SEQ. ID. NO. 5). Primer PBR2 anneals downstream and corresponds to pBR322 3691–3720 (TCCCCCATGTTG TGCAAAAAAGCGGTTAGC) (SEQ. ID. NO. 6). These 30 mer oligos were purified by electroelution from a denaturing polyacrylamide gel. The primers are labeled in a kinase reaction using 10 µM primer, 50 mM Tris.HCl pH 7.5, 10 mM $MgCl_2$, 70 µCi [γ-³²P] ATP and 10 units T4 polynucleotide kinase for 30 minutes at 37° C. A final concentration of 0.2 µM (each) of these two labeled primers are combined with 200 ng of PstI/HincII digested pBR322. These are denatured at 98° C. for 3 minutes in a buffer containing 25 mM potassium phosphate pH 7.4, 2–8 mM $MgCl_2$, 0.2 to 1 mM dNTPs and cooled to the reaction temperature (50°–70° C.) for 2 minutes. One unit of the polymerase is added and the reaction is continued for 10 minutes. The reactions are stopped by addition of an equal volume of 95% formamide, 50 mM EDTA, bromophenol blue dye. Twenty-five microliters are electrophoresed over a 6% denaturing gel and the gel is exposed to autoradiographic film.

Example 2

Purification of Native Enzyme

Crude Purification

Growth of *Thermoanaerobacter thermohydrosulfuricus* Cells

A lyophilized culture of *Thermoanaerobacter thermohydrosulfuricus* strain JW102 was purchased from the Deutsche Sammlung von Mikroorganismen und Zellkulturen, GmbH (DSM). The growth medium used was Clostridium Thermohydrosulfuricum Medium (medium #61 in the DSM catalog of strains, 1993 edition) which consists of (per liter): 10 g tryptone, 10 g sucrose, 2 g yeast extract, 0.2 g $FeSO_4 7H_2O$, 0.2 g $Na_2SO_2$, 0.08 g $Na_2S_2O_3.5H_2O$ and 1 mg Resazurin. The culture was grown at 70° C. under anaerobic conditions. After growth, the media was cooled to approximately room temperature and the culture harvested by continuous flow centrifugation. Cell paste was stored at −80° C. prior to subsequent procedures.

Preparation of Extract

Frozen cell paste (5 grams) was combined with 100 ml of buffer A (50 mM Tris.HCl pH 8.0, 10 mM NaCl, 1 mM DTT, 1 mM EDTA, 10% (w/v) glycerol). The paste was stirred at room temperature until resuspension was complete. The resulting cell suspension was cooled to 0° C. by incubation in an ice bath and subjected to approximately 5 minutes of sonication to lyse the cells. Cell debris was removed by centrifugation at 70,000×g for 20 minutes at 4° C. The supernatant cleared lysate was designated fraction 1.

Liquid Chromatography Purification

Fraction 1 was loaded onto a low-pressure liquid chromatography column (70 ml bed volume, 26 mm ø) of DEAE cellulose (DE-52, Whatman) equilibrated with buffer A. The column was washed with several column volumes of buffer A and the DNA polymerase eluted with a linear salt gradient from 10 mM to 1000 mM NaCl in buffer A at a flow rate of 0.9 ml/min. This and all subsequent chromatography steps were carried out at ambient room temperature (approximately 25° C.). The peak of activity eluted at approximately 32 mM NaCl. Active fractions were pooled and designated fraction 2.

Fraction 2 was loaded directly onto a column (22 ml bed volume, 16 mm ø) of heparin sepharose (Heparin Sepharose CL-6B, Pharmacia) equilibrated with buffer A. The column was washed with several column volumes of buffer A and the DNA polymerase activity eluted with a linear salt gradient from 10 mM to 700 mM NaCl in buffer A at a flow rate of 0.4 ml/min. The peak of activity eluted at approximately 400 mM NaCl. Active fractions were pooled and designated fraction 3.

Fraction 3 was loaded directly onto a column (2 ml bed volume, 16 mm ø) of hydroxylapatite (BioGel HA, Bio-Rad) equilibrated with buffer B (50 mM potassium phosphate pH 7.4, 1 mM DTT, 10% (w/v) glycerol). The column was washed with several column volumes of buffer B and the DNA polymerase eluted with a linear gradient from 50 mM to 700 mM potassium phosphate in buffer A at a flow rate of 0.4 ml/min. The DNA polymerase containing fractions were pooled and concentrated by ultrafiltration (Centricon-50, Amicon) to a volume of 100 ml to which 100 ml of 100% glycerol was added to obtain the final product. This final preparation was determined to contain about 1000 units of DNA polymerase which was judged to be approximately 80% pure on a coomasie stained denaturing polyacrylamide gel (SDS-PAGE).

Optimized Purification
Preparation of Extract

Frozen cell paste (45 grams) was resuspended in 250 ml of lysis buffer (50 mM Tris.HCl pH 8, 10 mM NaCl, 5 mM EDTA, 0.2% (v/v) NP40, 1 mM DTT). Lysozyme was added to 200 mg/ml final concentration and the solution was stirred at room temperature for 60 min. DNase I was added to 10 mg/ml final concentration and incubation was continued for 10 minutes. Insoluble material was removed by ultracentrifugation at 70,000×g for 40 min. The decanted supernatant is designated fraction I.

Polyethyleneimine Precipitation

A pilot polyethyleneimine (PEI) precipitation experiment was done to determine the final PEI concentration for this lysate to precipitate all polymerase activity with the least coprecipitate protein content. PEI was added from a 10% (v/v) stock to Fraction I to 0.4% final concentration. The solution was stirred for 20 minutes at 4° C. The PEI precipitate was collected by centrifugation at 8,000×g for 20 minutes. The polymerase activity was extracted from the pellet with 150 ml of 300 mM NaCl in buffer A (50 mM Tris.HCl pH 8, 1 mM DTT, 1 mM EDTA and 10% glycerol). This solution was centrifuged again at 17,000×g. Ammonium sulfate was added to the supernatant to 80% saturation and the solution was stirred for one hour at 4° C. to precipitate proteins from residual PEI. The ammonium sulfate fraction was centrifuged at 48,000×g for 30 min and the pellet resuspended in 400 ml 10 mM NaCl, 50 mM Tris.HCl pH 8. This is designated Fraction II.

Liquid Chromatography Purification

A column (150 ml bed volume) of Heparin-Sepharose CL-6B (Pharmacia) was equilibrated with 150 mM NaCl in buffer A. Fraction II was loaded at 150 ml/h and washed with two bed volumes of buffer A. The polymerase activity was then eluted with a linear gradient of 150 mM to 700 mM NaCl in buffer A yielding a polymerase peak at about 400 mM NaCl. The peak fractions were pooled and diluted fivefold with 100 mM NaCl in buffer B (50 mM Tris.HCl pH 7.5, 0.1 mM DTT, 1 mM EDTA and 5% glycerol). This pool is designated Fraction III.

A column (4 ml bed volume) of ssDNA agarose (Pharmacia) was equilibrated with 100 mM NaCl in buffer B. One-third of the Fraction III was loaded at a flow rate of 12 ml/hr. The column was washed with the same buffer and polymerase activity eluted with a linear gradient of 100 mM to 1000 mM NaCl in buffer B. The polymerase activity peak eluted at approximately 375 mM NaCl. The peak fractions were pooled and concentrated with Centricon-50 (Amicon) and stored by adding an equal volume of 100% glycerol.

Preparation of exo-Enzyme by Subtilisin Cleavage

Approximately 850 units of purified native *Thermoanaerobacter thermohydrosulfuricus* DNA polymerase I was exchanged into 150 mM potassium phosphate pH 6.5 by three rounds of dilution in this buffer and concentration by ultrafiltration yielding a solution containing about 250 mg of protein in 550 µl. Subtilisin (10 µl of 0.06 mg/ml solution) was added to the polymerase and the mixture was incubated at 37° C. for 1 hour. After incubation, the reaction was diluted to 10 ml final volume with buffer A and loaded onto a column of heparin sepharose (4 ml bed volume, 16 mm ⌀) equilibrated in buffer A containing 150 mM NaCl. The column was washed with several column volumes of this buffer and the polymerase activity eluted with a linear gradient of 150 mM to 700 mM NaCl in buffer A. Active fractions were pooled.

Example 3

Characterization of Native Enzyme
General properties

The native enzyme migrates as an approximately 90,000 Da polypeptide (just below phosphorylase B) on SDS-PAGE. The enzyme possesses strand displacement activity. It possesses a 5'-3' exonuclease activity at approximately 1/80 the level of polymerase activity (unit:unit). The temperature optimum of DNA synthesis is near 75° C. under assay conditions. The optimum $Mg^{2+}$ concentration of DNA synthesis is 1 mM. The optimum $Mn^{2+}$ concentration of DNA synthesis is 0.5 mM.

Assay for thermal stability

To assess the thermal stability of the enzyme, a sample of native *Thermoanaerobacter thermohydrosulfuricus* DNA polymerase was incubated at elevated temperatures in several buffers. The buffers all consisted of 25 mM Tris.HCl pH 8.5, 50 mM KCl, 5 mM $MgCl_2$, 1 mM 2-mercaptoethanol, 0.5% (w/v) Nonidet P-40 and 100 mg/ml BSA with the following additions:

BSA buffer: no additions.

GLY buffer: add glycerol to 40% (v/v)

MMO buffer: add N-methylmorpholine-N-oxide (MMO) to 3M

TMANO buffer: add Trimethylamine-N-oxide (TMANO) to 4M

Native enzyme (0.02 units/µl) was incubated in these buffers at various temperatures. At 5, 10 and 15 minutes, 5 µl aliquots were withdrawn and placed into a fresh tube on ice. When all samples had been acquired, the heated aliquots were assayed in the usual manner. Results are expressed as the fraction activity remaining at a given time point at a given temperature.

The enzyme was least stable in BSA buffer, retaining half the initial measured polymerase activity after about 5 minutes at 80° C. In GLY buffer, the enzyme retained half the initial activity after about 5 minutes at 85° C. In MMO and TMANO buffers, incubation at 85° to 90° C. was required to eliminate half the initial measured activity in 5 minutes. Incubation in any of the these buffers at 75° C. for 15 minutes resulted in not more than 20% loss of initial DNA polymerase activity.

Example 4

Characterization of Subtilisin-Cleaved Enzyme
General properties

The cleaved enzyme migrates as a doublet consisting of polypeptides migrating at approximately 64 kDa and 55 kDa on SDS-PAGE. It is free of detectable exonuclease activity. The enzyme possesses strand displacement activity. The enzyme has similar thermal stability to the native enzyme.

Example 5

Preparation of Cloned 64 kDa Enzyme
Preparation of genomic DNA

Frozen cell paste of *Thermoanaerobacter thermohydrosulfuricus* (approximately 350 mg) was resuspended in 700 µl of lysis buffer (50 mM Tris.HCl pH 8.0, 50 mM EDTA, 3% SDS (w/v), 1% 2-mercaptoethanol (v/v)) and incubated for 1 hour at 65° C. This solution was extracted three times with 25:24:1 phenol:chloroform:isoamyl alcohol, twice with chloroform and precipitated with two volumes of 100% ethanol. The pellet was dried briefly in vacuo and dissolved in 700 µl TE (10 mM Tris.HCl pH 8.0, 1 mM EDTA). The concentration of genomic DNA was determined spectrophotometrically by measuring the absorbance at 260 nm ($1A_{260}$=50µg/ml) and by comparison of UV fluorescence of bands on an ethidium bromide stained agarose gel relative to standard concentration markers.

Preparation of DNA polymerase I specific probe Genomic DNA was used as a substrate for a PCR reaction using degenerate oligonucleotides designed against conserved regions of DNA polymerase I. family polymerases (Uemori, T., Ishino, Y., Fujita, K., Asada, K. and Kato, I. (1993) *J. Biochem.* 113, 401–410). A standard Taq PCR reaction (20 µl) contained about 1 ng genomic DNA and 1 mM of each primer EPOLF (GACCC(ATC)AAC(CT)T(CG)CA(AG)A A(CT)AT(ATC)CC (SEQ.ID.NO. 7) and EPOLR ((GT)A (CG) (CG)A(GT) (CT)TC (AG) TCGTG(GATC)AC(CT) TG) (SEQ. ID. NO. 8). After one round of PCR, the product was resolved on an agarose gel. The product around the expected 600 bp region was excised from the gel, crushed, soaked in TE and used as substrate for a second round of PCR using the same conditions. The resulting ca. 600 bp product was directly sequenced using the EPOLF and EPOLR primers (Sequenase PCR Product Sequencing Kit, Amersham). One open reading frame was found to be homologous to the targeted region of DNA polymerases I of known sequence as judged by BLAST analysis.

Preparation of subgenomic libraries and screening

This PCR product was labeled using a radioactive or non-radioactive hybridization kit (Gene Images, USB) and used to probe blots of agarose gels of genomic DNA digested with various restriction enzymes. Digestion of genomic DNA with HindIII produced a unique hybridizing fragment of approximately 1.7 kb. DNA fragments of approximately 1.7 kb were excised from an agarose gel and cloned into pBluescript II KS (+) (Stratagene). Individual colonies that hybridized to the probe were purified and sequenced. Similarly, double digestion of *Thermoanaerobacter thermohydrosulfuricus* genomic DNA with EcoRI and XhoI produced a unique hybridizing fragment of approximately 1.9 kb and digestion with EcoRI produced a unique hybridizing fragment of approximately 3 kb. The sequences of these clones were merged and formed a coherent open reading frame which had high homology to the C-terminal portion DNA polymerases I of known sequence as judged by BLAST analysis. The clone containing the 1.7 kb HindIII fragment was digested with EcoRI and XhoI to produce a 1.4 kb fragment which was gel purified, $^{32}$P labeled by nick-translation and used to probe a blot of *Thermoanaerobacter thermohydrosulfuricus* genomic DNA digested with PstI and XhoI. This identified a unique hybridizing fragment of 3 kb that contained the remaining N-terminal portion of the gene. The nucleotide sequence is presented in FIGS. 1A–E (SEQ. ID. NO. 1) and a contiguous open reading frame potentially encoding the native polymerase is presented in FIGS. 2A–D (SEQ. ID. NO. 2).

Preparation of expression vectors

Several PCR products were made from the genomic DNA that allowed cloning portions of polymerase coding sequence not including 5'-3' exonuclease domain (See FIG. 5). Letters A–D represent start sites of the various constructs outlined in the table below These truncated polymerase coding sequences were placed under the control of the λ $P_L$ promoter of the expression vector pRE2 (Reddy, P., Peterkofsky, A. and McKenney, K. (1989) *Nucleic Acids Res.* 17, 10473–10488). These vectors were propagated in *E. coli* strain DH-1 λ+(λcI+).

To minimize errors introduced by Taq DNA polymerase in PCR, a modified long PCR was carried out. The PCR reaction contained: 20 mM Tricine (pH 8.8), 85 mM KOAc, 200 mM each dNTP, 5% DMSO, 0.5 mM each primer, 1.5 mM MgOAc (added as Hot-Start), 2.5 units Hot Tub (or rTth) DNA polymerase per 100 ml reaction (Amersham), 0.025 U Deep Vent DNA (New England Biolabs) polymerase per 100 µl reaction, 20–100 ng *Thermoanaerobacter thermohydrosulfuricus* genomic DNA per 100 µl reaction. The cycling parameters consisted of: 94° C. 30 s, then 68° C. 10 m40 s×8 cycles; 94° C. 30 s, then 68° C. 12 m00s×8 cycles; 94° C. 30 s, then 68° C. 13 m20 s×8 cycles; 94° C. 30 s, then 68° C. 14 m40 s×8 cycles.

All PCR products were generated with the reverse primer DDREV(GGGGTACCT CTAGATCACTTGGCCAAAAACCA) (SEQ. ID. NO. 9) at the 3' end and various primers utilized at the 5' end:

DDMET
 (GGAATTCCATATGGCTTACCTGCTGAACCCGTC TGAGTCTAAC) (SEQ. ID. NO. 10);

DD55kd
 (GGAATTCCATATGGCTCTTTCTTATAAAGGAAT AGAG) (SEQ. ID. NO. 11);

DD64kd
 (GGAATTCCATATGAAAGTTGAAAAATGGTCA) (SEQ. ID. NO. 12);

DD64pref
 (GGAATTCCATATGAAAGTTGAAAAATGGTCTA AAGTAGACATCAAAGAAT TAG) (SEQ. ID. NO. 13);

DDHF
 (GGAATTCCATATGAAGCTTTTAGAGCTTTT) (SEQ. ID. NO. 14);

DD67kd
 (GGAATTCCATATGAAACTTTTAGAGCTTTTCAA CAAATTAGAATTC) (SEQ. ID. NO. 15).

The resultant PCR products were digested with NdeI and KpnI and cloned into pRE2 digested with the same restriction enzymes.

Silent changes (see Table below) denotes that the 5' primer encodes some codons which are synonymous to the native sequences, but are more frequently utilized by *E. coli*. By this method, six different clones were constructed which encode four different polypeptides.

| Site | Plasmid | MW | codons | 5' Primer | Note |
| --- | --- | --- | --- | --- | --- |
| D | pMET11 | 55 kDa | 483 | DDMET | Silent changes, native MET |
| C | pRED5504 | 58 kDa | 502 | DD55kd | Native sequence + MET |
| B | pRED6404 | 64 kDa | 579 | DD64kd | Native sequence + MET |
| B | pPREF2 | 64 kDa | 579 | DD64pref | Silent changes + MET |
| A | pRED4 | 67 kDa | 609 | DDHF | Native sequence + MET |
| A | pRED6706 | 67 kDa | 609 | DD67kd | Silent changes + MET |

Expression of Cloned 64 kDa Enzyme

*E. coli* strain MZ-1 (cI857 lysogen) harboring the plasmid pRED6404 was cultured in LB medium (per liter: 10 g tryptone, 5 g yeast extract, 10 g NaCl) supplemented with 50 µg/ml ampicillin. The culture was grown at 30°–32° C. until the $OD_{600}$ reached 1.5 at which time the culture temperature was raised to 40°–42° C. Growth continued at this temperature for 2 hours before the culture was harvested in a continuous flow centrifuge. Cell paste was stored at −80° C. prior to subsequent procedures.

Example 6

Preparation of Cloned Full-length Enzyme

Full length enzyme was cloned by PCR from the clone of genomic DNA (SEQ. ID. NO. 1) (FIGS. 1A–E). A 5' primer DDF-FOR (GGAATTCCATATGGCTTATAAATTTTTAATCATTGAT GGTAGTAGC) (SEQ. ID. NO. 24) was synthesized. This primer encodes an Nde I site, inserts an alanine codon after the initiating methionine and changes two codons to synonymous codons favored by *E. coli* (ATA→ATC, Ile at aa position 6 and GGA→GGT, Gly at aa position 9). This primer was used in conjunction with a vector primer from the assembled clone of genomic DNA to produce a PCR product which was subsequently digested with Nde I and Xho I and sublconed into similarly digested pRED6404 to form pLS-3. The DNA for the full length enzyme is shown in FIGS. 7A-C (SEQ. ID. NO. 23).

Example 7

Purification of Cloned 64 kDa Enzyme

Preparation of Extract

Frozen cell paste (370 grams) was combined with 1800 ml of buffer A (50 mM Tris.HCl pH 8.0, 10 mM NaCl, 1 mM DTT, 1 mM EDTA, 10% (w/v) glycerol). The paste was stirred at room temperature until resuspension was complete. The cells were lysed using a French pressure cell. Cell debris was removed by centrifugation at 70,000×g for 20 minutes at 4° C.

Liquid chromatography purification

The cleared lysate was passed through a column of DEAE cellulose at 300 mM salt. The collected flow through was heated to 70° C. for 10 minutes, cleared again by centrifugation and loaded onto a column heparin sepharose. The DNA polymerase was eluted from this column with a salt gradient as before and was found in most cases to be pure. If not, column chromatography on hydroxylapatite was performed.

Example 8

Characterization of Cloned 64 kDa Enzyme

General properties

Cloned enzyme refers to the purified gene product of pRED6404. The cloned enzyme migrates as an approximately 64,000 Da polypeptide (just below bovine serum albumin, MW 67,000) on SDS-PAGE. The specific activity of the cloned enzyme is 28,000 units/mg. It is free of detectable exonuclease activity. The temperature optimum of DNA synthesis is near 72° C. under assay conditions. The optimum $Mg^{2+}$ concentration of DNA synthesis is 2 mM. The optimum $Mn^{2+}$ concentration of DNA synthesis is 0.7 mM.

Reverse transcriptase activity

The cloned enzyme functioned as a reverse transcriptase in an assay containing poly(rA):oligo($dT_{12-18}$) and [$^3$H]TTP at 42° C. This enzyme has RT activity in the presence of $Mg^{2+}$ with or without the addition of $Mn^{2+}$.

Measurement of reverse transcriptase activities of different enzymes using an SPA format Amersham reverse transcriptase scintillation proximity assay (SPA) kit (NK9020), and MMLV (E 70456), and AMV (E 70041) enzymes were supplied by Amersham International. The cloned 64 kD enzyme prepared above was designated as USB enzyme. Tth (N808-0098) enzyme was obtained from Perkin-Elmer.

MMLV and AMV enzymes were tested at 37° C. and 42° C. respectively in the presence of magnesium. The Tth and USB enzymes were both used at 60° C. with manganese present as the co-factor. The assay buffer used was the same as supplied in the SPA kit except the appropriate co-factor was substituted in the buffer mix. Essentially, the assay was set up as follows in duplicate using the protocol provided in the SPA kit in sarstedt tubes in a total reaction volume of 100 µl.

80 µl of 0.77 µM [$^3$H]TTP in a buffer consisting of:

50 mM Tris.HCl pH 8

80 mM KCl 10 mM $MgCl_2$ or 4 mM $MnCl_2$ 10 mM DTT 0.05% w/v NP40

10 µl of 0.2 µM primer/template (biotinylated ($dT_{16}$) oligonucleotide annealed to poly r(A)) in 10 mM Tris.HCl pH 8

1 mM $MgCl_2$

10 µl of 1 unit (as defined by the manufacturer) of enzyme diluted in 50 mM Tris.HCl pH 8, 10 mM DTT was added to each tube to start the reaction and incubated at the indicated temperature for 30 minutes after which the reaction was terminated with the addition of 10 µl 0.56M EDTA pH 8. 10 µl of the supplied streptavidin SPA beads were then added to each tube, and after incubating for a further 10 minutes at room temperature, were counted in a LKB 1205 scintillation counter.

Appropriate controls without enzyme were also performed. The data obtained is shown in FIG. 6. This experiment does not take into account the melting temperature of the primer used in this experiment which at 60° C. would theoretically leave only a minority of the primer still being annealed to the template. This may actually result in an underestimate of the activity observed with the USB and Tth enzymes.

Use of 64 kDa polymerase in Strand Displacement Amplification

The exonuclease deficient cloned enzyme described above was used in a Strand Displacement Amplification (SDA) reaction (Walker et al., (1992) *Proc. Natl. Acad. Sci. USA* 89:392–396). The target DNA to be amplified is a 1.2 kb clone of the insertion element IS 6110 from *Mycobacterium tuberculosis* [GenBank accession no. M29899]. The target DNA is cloned into pBluescript KS (Stratagene, La Jolla, Calif.). The reaction mixture (final concentrations: 25 mM potassium phosphate pH 7.4, 0.1 µg/ml BSA, 0.05 µM each primers B1 (CGATCGAGCAAGCCA) (SEQ. ID. NO. 16) and B2 (CGAGCCGCTCGCTGA) (SEQ. ID. NO. 17), 0.5 µM each primers S1.1 (ACCGCATCGAATGCATGTCTCGGTAGGCG ACTCGACC) (SEQ. ID. NO. 18) and S2.2 (CGATTCCGCTCAGACTTCTCGGGT TACTGAGATCCCT) (SEQ. ID. NO. 19), 1.4 mM dCTPαS, 0.5 mM each dATP, dGTP and dCTP and $10^7$ copies of target plasmid) was heated to 100° C. for 3 minutes to denature the target and then placed at 55° C. After about 5 minutes at 55° C., enzyme mix was added (final concentrations: 35 Units 64 kD polymerase, 160 Units BsoBI restriction enzyme (New England Biolabs, Beverly, Mass.) and 6.9 mM $MgCl_2$ (total reaction volume 50 µl) and incubation was continued for 10 minutes. An equal volume of stop solution (95% formamide, 20 mM EDTA and 0.05% each bromophenol blue and xylene cyanol FF) was added and 5 µl of this was electrophoresed on a 10% denaturing polyacrylamide gel. DNA was visualized by staining with ethidium bromide. The 64 kDa polymerase produced the expected 105 nucleotide full length product (major product) and the expected 86 nucleotide nicked product (minor product).

Use of 64 kDa polymerase in RT-PCR

The 64 kD polymerase was used as a reverse transcriptase in conjunction with AmpliTaq in RT-PCR. Using rabbit globin mRNA as a template, $10^6$ copies were detectable under the following protocol. In a reaction volume of 100 µl, the following components were assembled: 1×PCR buffer (10 mM Tris.HCl pH 8.3, 50 mM KCl), 2 mM $MgCl_2$, 200 µM each dNTP, 100 U human placental RNAse inhibitor (Amersham), $10^6$ copies rabbit globin mRNA (BRL), 30 pmoles globin-down primer (TCAGTGGTATTTGTGAGCCAGGGCATTGGCCACAC CAGCCACCACCTTCT) (SEQ. ID. NO. 25), 15 pmole globin-up primer (ATCCCCCAAAACAGACAGAATGGTGCATCTGTCC) (SEQ. ID. NO. 26), 2.5 U AmpliTaq polymerase and 5 U 64 kD polymerase. The reaction was incubated at 65° C. for 30 minutes followed by 5 minutes at 95° C., 35 cycles of [95° C. for 1 minute, 65° C. for 1 minute, 70° C. for 2 minutes] followed by 72° C. for 5 minutes. The product was resolved on a 2% ethidium bromide stained agarose gel and the expected 463 bp product was observed.

Using total RNA from rat liver, an RT-PCR product from the albumin gene was detected from 250 ng of template using the following protocol. In a reaction volume of 100 μl, the following components were assembled: 1×PCR buffer (10 mM Tris.HCl pH 8.3, 50 mM KCl), 2 mM MgCl$_2$, 200 μM each dNTP, 100 U human placental RNAse inhibitor (Amersham), 250 ng rat liver RNA, 30 pmoles albumin-down primer (GTTCTCCTGGAAGGAGGTGCACATGGCCTC) (SEQ. ID. NO. 27), 15 pmole albumin-up primer (CACACAAGAGTGAGATCGCCCATCGGTTTAAGGA) (SEQ. ID. NO. 28), 2.5 U AmpliTaq polymerase and 40 U 64 kD polymerase. The reaction was incubated at 65° C. for 30 minutes followed by 5 minutes at 95° C., 35 cycles of [95° C. for 1 minute, 65° C. for 1 minute, 70° C. for 2 minutes] followed by 72° C. for 5 minutes. The product was resolved on a 2% ethidium bromide stained agarose gel and the expected 386 bp product was observed.

Example 9

Construction of FY DNA Polymerase from
*Thermoanaerobacter thermohydrosulfuricus*

Starting Material

DNA constructs that were used to generate the FY polymerase were as follows:

pRED6706 is an expression vector which encodes a polypeptide of 608 amino acids. After an engineered initiating methionine, the remaining 607 amino acids encoded represent the C-terminal portion of the DNA polymerase I obtainable from of *Thermoanaerobacter thermohydrosulfuricus*.

pRED6404 is an expression vector which encodes a polypeptide of 578 amino acids. After an engineered initiating methionine, the remaining 577 amino acids encoded represent the C-terminal portion of the DNA polymerase I obtainable from *Thermoanaerobacter thermohydrosulfuricus*.

pPREF2 encodes the same polypeptide as pRED6404, but has three silent mutations of the *Thermoanaerobacter thermohydrosulfuricus* sequence at codons 7, 10 and 11 to eliminate codons rarely utilized by *E. coli*.

All of these constructs are derived from expression vector pRE2 (*Nucleic Acids Res.* (1989) 17, 10473–88) which utilizes the λ P$_L$ promoter and λ cII ribosome binding site.

Construction of F412Y

*Thermoanaerobacter thermohydrosulfuricus* DNA polymerase was searched for the sequence (RXXXKXXXFXXXYG) (SEQ. ID. NO. 20) to locate the motif B or O-helix region. The sequence (RRAAKAVNFGIIYG) (SEQ. ID. NO. 21) was found at amino acid residues numbered 433 through 466 of the predicted pRED6706 gene product. A mutagenic oligonucleotide, DDFY (AAGGTCAGAAAGCCCATAATCGCTTATGCCATATAT TATG CCATAATTTACGGC) (SEQ. ID. NO. 22) was designed anti parallel to nucleotides 1315–1371 of the pRED6706 coding sequence except for the change (AAA-ATA) at nt 1325. This change corresponds to phenylalanine being changed to tyrosine in the expressed polymerase. This oligonucleotide also overlaps a unique XhoI restriction site at nucleotide 1361.

Oligonucleotide DDFY together with DD64pref (SEQ. ID. NO. 13) which is complementary to nucleotides 94–133 of the pRED6706 coding sequence, contains an NdeI restriction site, were used to direct PCR amplification and simultaneous mutagenesis of pRED6706. The resulting PCR product was digested with NdeI and XhoI, purified by agarose gel electrophoresis and ligated with the large fragment of similarly treated pRED6404. The ligated construct was used to transform competent *E. coli* strain DH1 λ+(λcI+). Clones yielding an appropriate restriction enzyme digestion pattern were sequenced to confirm the mutation. Spurious mutations were found in addition to the desired mutation in all clones examined, so an AflIII/KpnI restriction fragment containing exclusively the F412Y mutation (pRED6404 numbering) was subcloned in pRED6404 to yield pLS-1.

Example 10

Purification of F412Y DNA Polymerase

Plasmid pLS-1 was transformed into *E. coli* strain MZ-1 (λ cI857 lysogen). One liter of culture in LB medium containing 100 μg/ml Ampicillin was grown at 30° until OD$_{600}$=1.1. The temperature was raised to 42° C. and growth continued for 2 hours. The cells were harvested by centrifugation (4 g wet weight) and resuspended in 15 ml buffer A (SO mM Tris.HCl pH 8.0, 1 mM DTT, 1 mM PMSF, 1 mM EDTA, 10% (v/v) glycerol) containing 50 mM NaCl. The resuspension was sonicated four times for 30 seconds and the lysate was cleared by centrifugation. The cleared lysate was made 300 mM in NaCl and passed through a column of DEAE cellulose (65 ml bed volume) equilibrated in buffer A containing 300 mM NaCl. The flow through fraction (45 ml) was collected, heated to 70° C. for 15 minutes and cleared by centrifugation. The cleared supernatant was diluted with buffer A containing 50 mM NaCl to a total volume of 120 ml. This solution was loaded onto a column of heparin sepharose (70 ml bed volume) equilibrated with buffer A containing 150 mM NaCl. The column was washed with this same buffer and the activity eluted from the column with a linear salt gradient from 150 mM to 700 mM NaCl in buffer A. Active fractions judged to be greater than 90% pure by SDS-PAGE were pooled, concentrated by ultrafiltration and dialyzed against 50 mM phosphate 50% (v/v) glycerol. The sequence is provided in FIGS. 4A–C (SEQ. ID. NO. 4).

Other embodiments are within the following claims.

We claim:

1. An enzymatically active DNA polymerase having at least 80% identity in its amino acid sequence to the DNA polymerase of *Thermoanaerobacter thermohydrosulfuricus*.

2. The polymerase of claim 1 wherein said DNA polymerase has an exonuclease activity removed by having an N-terminal deletion to give between 540 to 582 amino acids.

3. The polymerase of claim 1 wherein said polymerase has the phenylalanine at position 706 replaced with tyrosine.

4. The polymerase of claim 1 wherein said polymerase has an exonuclease activity removed by having an N-terminal deletion to give between 540 to 582 amino acids and the phenylalanine at position 706 replaced with tyrosine.

5. The polymerase of claim 1 wherein said polymerase has an exonuclease activity removed by deleting up to one third of the amino acid sequence at the N-terminal and the phenylalanine at position 706 replaced with tyrosine.

6. The polymerase of claim 1, wherein said DNA polymerase has an exonuclease activity removed by deleting up to one third of the amino acid sequence at the N-terminal.

7. Purified nucleic acid encoding the DNA polymerase of any of claims 1, 2, 3, 4, 5 or 6 in a buffer.

8. Host cell comprising a vector containing a nucleic acid sequence encoding the DNA polymerase of any of claims 1, 2, 3, 4, 5 or 6.

9. A composition comprising a DNA polymerase of any of claims 1, 2, 3, 4, 5, or 6 and a thermostable restriction enzyme for use in strand displacement amplification.

10. Method for generating and amplifying a nucleic acid fragment by strand displacement utilizing a DNA polymerase having at least 80% identity in its amino acid sequence to the DNA polymerase of *Thermoanaerobacter thermohydrosulfuricus*.

11. The method of claim 10, wherein said DNA polymerase has an exonuclease, activity removed by having an N-terminal deletion to give between 540 to 582 amino acids.

12. Kit for strand displacement amplification of DNA comprising a DNA polymerase of any of claims 1, 2, 3, 4, 5 or 6 and a thermostable restriction enzyme.

13. Method for sequencing DNA whereby at least a part of the nucleotide base sequence of a DNA template can be determined comprising the step of generating chain terminated fragments from said DNA template with a DNA polymerase of any of claims 3, 4, or 5 in the presence of at least one chain terminating agent and determining the sequence of at least part of said DNA template from the sizes of said fragments.

14. Kit for sequencing DNA comprising a DNA polymerase of any of claims 3, 4, or 5 and a pyrophosphatase.

15. Method for preparing cDNA by providing an oligonucleotide primer, a polymerase of any of claims 1, 2, 3, 4, 5 or 6, and between one and four deoxyribonucleoside phosphates.

16. A DNA polymerase of claim 1, wherein said polymerase has a reverse transcriptase activity.

17. A DNA polymerase of claim 2 or 6, wherein said polymerase has a reverse transcriptase activity.

18. Method for reverse transcription/polymerase chain reaction utilizing a DNA polymerase of claim 1 and a polymerase suitable for carrying out polymerase chain reaction in a single reaction vessel.

19. The method of claim 18, wherein said DNA polymerase of claim 1 has an exonuclease activity removed by having an N-terminal deletion to give between 540 to 582 amino acids.

20. The method of claim 18, wherein said polymerase suitable for carrying out polymerase chain reaction is *Thermus aquaticus* DNA polymerase.

21. Kit for reverse transcription/polymerase chain reaction comprising a DNA polymerase of claim 1 and a polymerase suitable for carrying out polymerase chain reaction.

22. The kit of claim 21, wherein said DNA polymerase of claim 1 has an exonuclease activity removed by having an N-terminal deletion to give between 540 to 582 amino acids.

23. The kit of claim 21, wherein said polymerase suitable for carrying out polymerase chain reaction is *Thermus aquaticus* DNA polymerase.

24. Solution for use in RT/PCR comprising DNA polymerase of claim 1 and a polymerase suitable for carrying out polymerase chain reaction.

25. The solution of claim 24, wherein said DNA polymerase of claim 1 has an exonuclease activity removed by having an N-terminal deletion to give between 540 to 582 amino acids.

26. The solution of claim 24, wherein said polymerase suitable for carrying out polymerase chain reaction is *Thermus aquaticus* DNA polymerase.

27. Solution for strand displacement amplification of DNA comprising a DNA polymerase of claims 1, 2, 3, 4, 5 or 6 and a thermostable restriction enzyme.

28. Solution for sequencing DNA comprising a DNA polymerase of any of claims 3, 4, or 5 and a pyrophosphatase.

29. A stable enzymatic composition comprising a purified DNA polymerase of any of claims 1, 2, 3, 4, 5 or 6 in a buffer.

30. The method of claim 10, wherein said DNA polymerase has an exonuclease activity removed by deleting up to one third of the amino acid sequence at the N-terminal.

31. The method of claim 18, wherein said DNA polymerase of claim 1 has an exonuclease activity removed by deleting up to one third of the amino acid sequence at the N-terminal.

32. The kit of claim 21, wherein said DNA polymerase of claim 1 has an exonuclease activity removed by deleting up to one third of the amino acid sequence at the N-terminal.

33. The solution of claim 24, wherein said DNA polymerase of claim 1 has an exonuclease activity removed by deleting up to one third of the amino acid sequence at the N-terminal.

* * * * *

SEQUENCE LISTING ( 1 ) GENERAL INFORMATION:

( i i i ) NUMBER OF SEQUENCES: 28

( 2 ) INFORMATION FOR SEQ ID NO: 1:

( i ) SEQUENCE CHARACTERISTICS:
( A ) LENGTH: 5300 base pairs
( B ) TYPE: nucleic acid
( C ) STRANDEDNESS: single
( D ) TOPOLOGY: linear ( x i ) SEQUENCE DESCRIPTION: SEQ ID NO: 1:

| | | | | | | |
|---|---|---|---|---|---|---|
| CTGCAGAAAA | AAATAATAAA | AAGTTTAAAA | AATATGCCTC | CTATAGAACT | TCCTGAAGAT | 60 |
| TTAATAAAA | AATTACATCA | AAAATTGATT | TATCATAAAA | ATTTTTTAGA | GAAGAAAAA | 120 |
| GAAAGGCTAA | AAAAGACGTT | TAACAATAGT | AGCTATTGCG | ACATCTTTAA | TATTTATGAC | 180 |
| AGTATTTATA | GTGAATACAT | TTAATAAATC | CTTACAAATT | GAGTCTAATA | CTCCTTTAGC | 240 |
| TAACATTGAA | ATGGGACAGA | GTTATGGCTT | ACCTCAGAAA | GAAGGAGCTA | ATAATGAAAG | 300 |
| AGGATTGCCA | GCAGGAACTT | CAAGGAAAAT | TACAAAGAAT | GCAACCATTT | CCTTGGAAGT | 360 |
| AGAAGACGTC | AATGGATGTT | ATGATAAAGT | CTTTCAGTTA | GTAAAGAAG | CAGAAGGTTT | 420 |
| TATTGAAACT | TCTGAGGAAA | CAGTATCCAG | TGATAATATC | AAAAGGGTAA | ATGTTGTTTT | 480 |
| GAAGGTGCGG | GAAGATAAAT | TTGAAAGTGT | GATTTCTCAA | ATTAAAGATT | TGGCAAAGTA | 540 |
| ACAGCTTTAA | GGATTGACAG | CAAAGACATT | ACAGACCAGT | ATTATGACTT | ACAAGCAAGG | 600 |
| CTAAAAAATT | TGGAAGTAGA | GGAACAAAAG | CTTCAAGACA | TCATGAATAA | GGCTACTACA | 660 |
| GTCAAGGAAA | TGCTTGAAGT | AGAATCTGAA | ATAAACAGGA | TAAGAAGTGA | AATAGAGTCA | 720 |
| ATGGAAGGAC | AGCTAAAATT | ATGGGAAAAT | CTTACGAGTC | TGGCAACCAT | AAATCTTTCA | 780 |
| ATAAAAGAGA | TACCTAAAGA | TGAGAAACCT | TTGGCTATAG | TTTCTTTTAA | GGGAATTGGT | 840 |
| AAAGGTATAA | AAGAAGCATT | TATAAATAAT | ATGAATTTTT | TAATATTTTT | TATGAAAAAG | 900 |
| TTGATAATAA | TATTGGTGAT | AATTTTGCCT | TATAGTGTAC | TGGCTTTAAT | CGGTTATAAA | 960 |
| GTGTATATCT | ATTTCAAAAA | AAGGAGATGA | CAATTACAT | CTTCTTTTTT | TTGCGGTATA | 1020 |
| TTAAAATACA | AAGAAATAAA | AATGGGAGTG | ATTTAATGTA | TAAATTTTTA | ATAATTGATG | 1080 |
| GAAGTAGCCT | CATGTACAGA | GCCTATTATG | CCTTGCCCAT | GCTTACTACA | AGTGAGGGAT | 1140 |
| TGCCTACAAA | TGCTCTGTAT | GGTTTTACTA | TGATGCTTAT | AAAACTTATC | GAGGAGGAAA | 1200 |
| AACCTGATTA | CATAGCTATT | GCTTTTGACA | AAAAAGCTCC | TACTTTTAGA | CACAAAGAAT | 1260 |
| ATCAAGACTA | CAAAGCTACA | AGACAAGCTA | TGCCTGAAGA | ACTTGCTGAA | CAAGTAGACT | 1320 |
| ATTTGAAAGA | AATTATAGAT | GGCTTTAATA | TAAAGACATT | AGAATTAGAA | GGTTATGAAG | 1380 |
| CTGATGACAT | TATAGGGACT | ATTTCAAAGC | TGGCAGAGGA | AAAAGGAATG | GAAGTGCTTG | 1440 |
| TAGTTACAGG | AGACAGAGAT | GCTCTTCAAT | TAGTTTCAGA | TAAAGTGAAG | ATAAAAATTT | 1500 |
| CTAAAAGGG | TATTACTCAG | ATGGAAGAGT | TGACGAAAA | GGCTATTTTA | GAAAGGTATG | 1560 |
| GAATAACTCC | TCAGCAGTTT | ATAGATTTAA | AAGGGCTTAT | GGGAGATAAA | TCTGATAATA | 1620 |
| TCCCTGGAGT | ACCTAATATA | GGGGAAAAAA | CTGCGATTAA | GCTATTAAAG | GATTTTGGAA | 1680 |
| CAATTGAAAA | TTTAATCCAA | AATCTTTCTC | AGCTTAAAGG | TAAAATAAAA | GAAAATATAG | 1740 |
| AAAACAATAA | AGAGTTAGCT | ATAATGAGTA | AGAGGCTTGC | TACTATAAAA | AGAGACATTC | 1800 |
| CCATTGAGAT | AGATTTTGAG | GAGTATAAAG | TAAAAAAATT | TAATGAGGAG | AAGCTTTTAG | 1860 |

```
AGCTTTTTAA TAAATTAGAA TTCTTTAGTT TAATTGATAA CATAAAGAAA GAAAGTAGCA   1920
TAGAGATTGT AGATAATCAT AAAGTTGAAA AATGGTCAAA AGTAGATATA AAAGAATTAG   1980
TAACTTTGTT GCAAGATAAC AGAAATATTG CTTTTTACCC GTTAATTTAT GAAGGGAAA    2040
TAAAAAAAAT AGCCTTTTCT TTTGGAAAGG ATACGGTTTA TATTGACGTT TTCCAAACAG   2100
AAGATTTAAA GGAGATTTTT GAAAAGAAG ATTTTGAATT TACAACCCAT GAAATAAAGG    2160
ATTTTTTAGT GAGGCTTTCT TATAAAGGAA TAGAGTGTAA AAGCAAGTAC ATAGATACTG   2220
CTGTAATGGC TTATCTTCTG AATCCTTCTG AGTCTAACTA TGACTTAGAC CGTGTGCTAA   2280
AAAAATATTT AAAGGTAGAT GTGCCTTCTT ATGAAGGAAT ATTTGGCAAA GGTAGGGATA   2340
AAAAGAAAAT TGAAGAGATT GACGAAAACA TACTTGCTGA TTATATTTGC AGTAGATGTG   2400
TGTATCTATT TGATTTAAAA GAAAAGCTGA TGAATTTTAT TGAAGAGATG GATATGAAAA   2460
AACTTCTATT AGAAATAGAA ATGCCTCTTG TAGAAGTTTT AAAATCAATG GAGGTAAGTG   2520
GTTTTACATT GGATAAAGAA GTTCTAAAAG AGCTTTCACA AAAGATAGAT GATAGAATAG   2580
GAGAAATACT AGATAAAATT TATAAAGAGG CAGGATATCA ATTAATGTA AATTCACCTA    2640
AGCAATTAAG TGAATTTTTG TTTGAAAAGT TAAACTTACC AGTAATAAAG AAAACAAAAA   2700
CAGGATACTC TACGGATTCT GAAGTTTTGG AACAATTGGT TCCTTATAAT GATATTGTCA   2760
GCGATATAAT AGAGTATCGG CAACTTACAA AACTTAAATC TACTTATATA GATGGATTTT   2820
TGCCTCTTAT GGATGAAAAC AATAGAGTAC ATTCTAATTT TAAACAAATG GTTACTGCTA   2880
CAGGTAGAAT AAGCAGCACC GAGCCAAATC TACAAAATAT ACCTATAAGA GAAGAGTTTG   2940
GCAGACAAAT TAGAAGGGCT TTTATTCCGA GGAGTAGAGA TGGATATATT GTTTCAGCAG   3000
ATTATTCTCA GATTGAACTG AGGGTTTTAG CACATGTTTC GGGAGATGAA AAGCTAATAG   3060
AATCTTTTAT GAATAATGAA GATATACATT TAAGGACAGC TTCGGAGGTT TTTAAAGTTC   3120
CTATGGAAAA AGTTACACCG GAGATGAGAA GAGCAGCAAA AGCCGTAAAT TTTGGCATAA   3180
TATATGGCAT AAGCGATTAT GGGCTTTCTC GAGACCTTAA AATATCAAGA AAAGAAGCAA   3240
AAGAGTACAT AAATAATTAT TTTGAAAGAT ATAAAGGAGT AAAAGATTAT ATTGAAAAAA   3300
TAGTACGATT TGCAAAAGAA AATGGCTATG TGACTACAAT AATGAACAGA AGGAGATATA   3360
TTCCTGAAAT AAACTCAAGA AATTTACTC AAAGATCGCA GGCCGAAAGG TTAGCAATGA    3420
ATGCTCCGAT ACAGGGAAGT GCGGCTGATA TAATAAAAAT GGCAATGGTT AAGGTATACA   3480
ACGATTTAAA AAAATTAAAG CTTAAGTCTA AGCTTATATT GCAAGTTCAT GACGAGCTTG   3540
TAGTGGATAC TTATAAGGAT GAAGTAGATA TCATAAAAAA GATACTTAAA GAAAATATGG   3600
AAAATGTAGT GCAATTAAAA GTTCCTCTGG TTGTTGAAAT TGGCGTAGGG CCTAATTGGT   3660
TTTTGGCCAA GTGAGGTGTG CAAAAATGCA AGTAATTGGA CTTACTGGCG GCATTGCCTC   3720
AGGTAAAAGT ACTGTATCCA AGCTATTAAA AAAGATGGGA GCTGTGGTAA TTGATGCAGA   3780
TATTGTATCA AGAGAAATAA TGGTAAAAGG AACAGAAGCA TATAATAGAA TTGTAGAATA   3840
TTTTGGAAAA GAAATTTTAA AGGAAGACGG CGAAATTGAC AGAAAGAAAT TAGGCAATAT   3900
TGTGTTTGCT GACAGAAAAA AGCTTAAAAA ACTAAATGAA ATTACTCATC CCATAATAAT   3960
AGAGAGGATA AAAGAAAAAA TAGAAGAAGA AAGAAAAAAA ATCAGCAAAA GGCAATTGTA   4020
TTAGATGCAG CTCTTTTAAT TGAGATGAAC TTTATAAATG GTAGATGAGG TTTGGTTAGT   4080
AGTAGTAGAC TCAAAAACTC AAATAAAGAG GGTTATGGAG AGGGATAAGC TTTCTTATAA   4140
GGATGCGATA AACCGAATAA AAAGCCAAAT GCTTTGGACG AAAAAATGAA GTACGCAGAT   4200
TTTATAATAA ACATAGCAAA GTTTTAAAGC TATGGAAAAA CAGTTACACT ATTTTGGGAA   4260
```

```
AGATTTGCAA CGTAAATTCA TGATATCGGA GGAGTTACTT TGAGAAAAAA AGTTGCGGCA     4320

ATTTTAATAC TATTAAGTTT ATTGTTTACT TACGAGTTAA ATACTCATTA TTTTTAAAA      4380

AAAATTTATC CTCGTAAATA CTATAATTAT GTATTTTATT ACGCAAAAGA GTATGGCATG     4440

GACCCCTATC TTATTTTTGC TGTGATAAAA GTCGAAAGTA ATTTAGAAG CGATGCAATT      4500

TCCAGCAAAA ATGCTAGAGG GTTAATGCAA ATTTACCAG AAACTGGAGA ATGGATTGCT      4560

AAAGAAATAG GGATAAAAAA TTACAGCAAT AGTATGCTTT TTGAACCTAA ATATAATATT     4620

CAAATGGGAA CGTGGTATTT GACTTATCTT CTTAAAACTT TTAATGGAAA TATTAAATTG     4680

GCTCTAGCGG CCTATAACGG AGGCAGTGGA AATGTAGATG CATGGCTTAA AGATAAAAGA     4740

TTTTCTAAAG ATGGTAAACA ACTACATATT GTTCCTTTTC CTGAGACAAA TAAATATATA     4800

AAAAAGGTAT TAGCAGTTTA CGAGATCTAT AAGTTCATAT ATGAAACTAA GAATTGATAT     4860

GAAGATTACT ATATACAAAA AAAGTTGAAA AATTGGTATA ATAGTATCGT TAAAAAGAAA     4920

ATAAAAGGG AGGACACAAA TGAAACCGTT GAAACATTTA AAAGACTTAA AGGAAGTAAA      4980

AATCGAAAGA GATAGGGAGT TTTTCTCAGC CACTCATGAA GAAATAAAAA ATGCTTGGAC     5040

TACAGATGTG TATTTTTTAA GAACCCAAGA TATTTTATCA TATCTTGGTG TACAGGATAA     5100

AATAGTTACT GCAGAGATAT TTCCAAGAAA AAAAGGAGTT TTTGCAGGAT TACCAGAAGT     5160

AATGAGTTTA CTTAAAGACA AAAATGTGGA AGTATGGTCT TTGAAAGAAG GAGATACTTT     5220

TGAAGCTAAA GATACGGTAA TGAGAATAAA AGGACCTTAT AGTGAATTTG GAATTTATGA     5280

AACGGCAATA TTAGGAATTC                                                 5300
```

( 2 ) INFORMATION FOR SEQ ID NO: 2:

( i ) SEQUENCE CHARACTERISTICS:
        ( A ) LENGTH: 872 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 2:

```
Met Tyr Lys Phe Leu Ile Ile Asp Gly Ser Ser Leu Met Tyr Arg Ala
 1               5                  10                  15

Tyr Tyr Ala Leu Pro Met Leu Thr Thr Ser Glu Gly Leu Pro Thr Asn
            20                  25                  30

Ala Leu Tyr Gly Phe Thr Met Met Leu Ile Lys Leu Ile Glu Glu Glu
        35                  40                  45

Lys Pro Asp Tyr Ile Ala Ile Ala Phe Asp Lys Lys Ala Pro Thr Phe
    50                  55                  60

Arg His Lys Glu Tyr Gln Asp Tyr Lys Ala Thr Arg Gln Ala Met Pro
 65                  70                  75                  80

Glu Glu Leu Ala Glu Gln Val Asp Tyr Leu Lys Glu Ile Ile Asp Gly
                85                  90                  95

Phe Asn Ile Lys Thr Leu Glu Leu Glu Gly Tyr Glu Ala Asp Asp Ile
            100                 105                 110

Ile Gly Thr Ile Ser Lys Leu Ala Glu Glu Lys Gly Met Glu Val Leu
        115                 120                 125

Val Val Thr Gly Asp Arg Asp Ala Leu Gln Leu Val Ser Asp Lys Val
    130                 135                 140

Lys Ile Lys Ile Ser Lys Lys Gly Ile Thr Gln Met Glu Glu Phe Asp
145                 150                 155                 160

Glu Lys Ala Ile Leu Glu Arg Tyr Gly Ile Thr Pro Gln Gln Phe Ile
                165                 170                 175
```

| | | | | | | | | | | | | | |
|---|---|---|---|---|---|---|---|---|---|---|---|---|---|
| Asp | Leu | Lys | Gly<br>180 | Leu | Met | Gly | Asp | Lys<br>185 | Ser | Asp | Asn | Ile | Pro<br>190 | Gly | Val |
| Pro | Asn | Ile<br>195 | Gly | Glu | Lys | Thr | Ala<br>200 | Ile | Lys | Leu | Leu<br>205 | Lys | Asp | Phe | Gly |
| Thr | Ile<br>210 | Glu | Asn | Leu | Ile | Gln<br>215 | Asn | Leu | Ser | Gln | Leu<br>220 | Lys | Gly | Lys | Ile |
| Lys<br>225 | Glu | Asn | Ile | Glu | Asn<br>230 | Asn | Lys | Glu | Leu | Ala<br>235 | Ile | Met | Ser | Lys | Arg<br>240 |
| Leu | Ala | Thr | Ile | Lys<br>245 | Arg | Asp | Ile | Pro | Ile<br>250 | Glu | Ile | Asp | Phe | Glu<br>255 | Glu |
| Tyr | Lys | Val | Lys<br>260 | Lys | Phe | Asn | Glu | Glu<br>265 | Lys | Leu | Leu | Glu | Leu<br>270 | Phe | Asn |
| Lys | Leu | Glu<br>275 | Phe | Phe | Ser | Leu | Ile<br>280 | Asp | Asn | Ile | Lys | Lys<br>285 | Glu | Ser | Ser |
| Ile | Glu<br>290 | Ile | Val | Asp | Asn | His<br>295 | Lys | Val | Glu | Lys | Trp<br>300 | Ser | Lys | Val | Asp |
| Ile<br>305 | Lys | Glu | Leu | Val | Thr<br>310 | Leu | Leu | Gln | Asp | Asn<br>315 | Arg | Asn | Ile | Ala | Phe<br>320 |
| Tyr | Pro | Leu | Ile | Tyr<br>325 | Glu | Gly | Glu | Ile | Lys<br>330 | Lys | Ile | Ala | Phe | Ser<br>335 | Phe |
| Gly | Lys | Asp | Thr<br>340 | Val | Tyr | Ile | Asp | Val<br>345 | Phe | Gln | Thr | Glu | Asp<br>350 | Leu | Lys |
| Glu | Ile | Phe<br>355 | Glu | Lys | Glu | Asp | Phe<br>360 | Glu | Phe | Thr | Thr | His<br>365 | Glu | Ile | Lys |
| Asp | Phe<br>370 | Leu | Val | Arg | Leu | Ser<br>375 | Tyr | Lys | Gly | Ile | Glu<br>380 | Cys | Lys | Ser | Lys |
| Tyr<br>385 | Ile | Asp | Thr | Ala | Val<br>390 | Met | Ala | Tyr | Leu | Leu<br>395 | Asn | Pro | Ser | Glu | Ser<br>400 |
| Asn | Tyr | Asp | Leu | Asp<br>405 | Arg | Val | Leu | Lys | Lys<br>410 | Tyr | Leu | Lys | Val | Asp<br>415 | Val |
| Pro | Ser | Tyr | Glu<br>420 | Gly | Ile | Phe | Gly | Lys<br>425 | Gly | Arg | Asp | Lys | Lys<br>430 | Lys | Ile |
| Glu | Glu | Ile<br>435 | Asp | Glu | Asn | Ile | Leu<br>440 | Ala | Asp | Tyr | Ile | Cys<br>445 | Ser | Arg | Cys |
| Val | Tyr<br>450 | Leu | Phe | Asp | Leu | Lys<br>455 | Glu | Lys | Leu | Met | Asn<br>460 | Phe | Ile | Glu | Glu |
| Met<br>465 | Asp | Met | Lys | Lys | Leu<br>470 | Leu | Leu | Glu | Ile | Glu<br>475 | Met | Pro | Leu | Val | Glu<br>480 |
| Val | Leu | Lys | Ser | Met<br>485 | Glu | Val | Ser | Gly | Phe<br>490 | Thr | Leu | Asp | Lys | Glu<br>495 | Val |
| Leu | Lys | Glu | Leu<br>500 | Ser | Gln | Lys | Ile | Asp<br>505 | Asp | Arg | Ile | Gly | Glu<br>510 | Ile | Leu |
| Asp | Lys | Ile<br>515 | Tyr | Lys | Glu | Ala | Gly<br>520 | Tyr | Gln | Phe | Asn | Val<br>525 | Asn | Ser | Pro |
| Lys | Gln<br>530 | Leu | Ser | Glu | Phe | Leu<br>535 | Phe | Glu | Lys | Leu | Asn<br>540 | Leu | Pro | Val | Ile |
| Lys<br>545 | Lys | Thr | Lys | Thr | Gly<br>550 | Tyr | Ser | Thr | Asp | Ser<br>555 | Glu | Val | Leu | Glu | Gln<br>560 |
| Leu | Val | Pro | Tyr | Asn<br>565 | Asp | Ile | Val | Ser | Asp<br>570 | Ile | Ile | Glu | Tyr | Arg<br>575 | Gln |
| Leu | Thr | Lys | Leu | Lys<br>580 | Ser | Thr | Tyr | Ile | Asp<br>585 | Gly | Phe | Leu | Pro<br>590 | Leu | Met |
| Asp | Glu | Asn | Asn | Arg | Val | His | Ser | Asn | Phe | Lys | Gln | Met | Val | Thr | Ala |

595                          600                          605
Thr Gly Arg Ile Ser Ser Thr Glu Pro Asn Leu Gln Asn Ile Pro Ile
    610                          615                     620

Arg Glu Glu Phe Gly Arg Gln Ile Arg Arg Ala Phe Ile Pro Arg Ser
625                     630                     635                          640

Arg Asp Gly Tyr Ile Val Ser Ala Asp Tyr Ser Gln Ile Glu Leu Arg
                645                          650                          655

Val Leu Ala His Val Ser Gly Asp Glu Lys Leu Ile Glu Ser Phe Met
            660                     665                     670

Asn Asn Glu Asp Ile His Leu Arg Thr Ala Ser Glu Val Phe Lys Val
        675                     680                     685

Pro Met Glu Lys Val Thr Pro Glu Met Arg Arg Ala Ala Lys Ala Val
    690                     695                     700

Asn Phe Gly Ile Ile Tyr Gly Ile Ser Asp Tyr Gly Leu Ser Arg Asp
705                     710                     715                          720

Leu Lys Ile Ser Arg Lys Glu Ala Lys Glu Tyr Ile Asn Asn Tyr Phe
                725                     730                     735

Glu Arg Tyr Lys Gly Val Lys Asp Tyr Ile Glu Lys Ile Val Arg Phe
            740                     745                     750

Ala Lys Glu Asn Gly Tyr Val Thr Thr Ile Met Asn Arg Arg Arg Tyr
        755                     760                     765

Ile Pro Glu Ile Asn Ser Arg Asn Phe Thr Gln Arg Ser Gln Ala Glu
770                     775                          780

Arg Leu Ala Met Asn Ala Pro Ile Gln Gly Ser Ala Ala Asp Ile Ile
785                     790                     795                          800

Lys Met Ala Met Val Lys Val Tyr Asn Asp Leu Lys Lys Leu Lys Leu
                805                     810                     815

Lys Ser Lys Leu Ile Leu Gln Val His Asp Glu Leu Val Val Asp Thr
            820                     825                     830

Tyr Lys Asp Glu Val Asp Ile Ile Lys Lys Ile Leu Lys Glu Asn Met
        835                     840                     845

Glu Asn Val Val Gln Leu Lys Val Pro Leu Val Val Glu Ile Gly Val
    850                     855                     860

Gly Pro Asn Trp Phe Leu Ala Lys
865                     870

( 2 ) INFORMATION FOR SEQ ID NO: 3:

( i ) SEQUENCE CHARACTERISTICS:
        ( A ) LENGTH: 608 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 3:

Met Lys Leu Leu Glu Leu Phe Asn Lys Leu Glu Phe Phe Ser Leu Ile
1               5                   10                      15

Asp Asn Ile Lys Lys Glu Ser Ser Ile Glu Ile Val Asp Asn His Lys
            20                  25                  30

Val Glu Lys Trp Ser Lys Val Asp Ile Lys Glu Leu Val Thr Leu Leu
        35                  40                  45

Gln Asp Asn Arg Asn Ile Ala Phe Tyr Pro Leu Ile Tyr Glu Gly Glu
    50                  55                  60

Ile Lys Lys Ile Ala Phe Ser Phe Gly Lys Asp Thr Val Tyr Ile Asp
65                  70                  75                      80

-continued

| | | | | | | | | | | | | | | |
|---|---|---|---|---|---|---|---|---|---|---|---|---|---|---|
|Val|Phe|Gln|Thr|Glu|Asp|Leu|Lys|Glu|Ile|Phe|Glu|Lys|Glu|Asp|Phe|
| | | | |85| | | |90| | | |95| | |
|Glu|Phe|Thr|Thr|His|Glu|Ile|Lys|Asp|Phe|Leu|Val|Arg|Leu|Ser|Tyr|
| | | |100| | | |105| | | | |110| | |
|Lys|Gly|Ile|Glu|Cys|Lys|Ser|Lys|Tyr|Ile|Asp|Thr|Ala|Val|Met|Ala|
| | | |115| | | |120| | | |125| | | |
|Tyr|Leu|Leu|Asn|Pro|Ser|Glu|Ser|Asn|Tyr|Asp|Leu|Asp|Arg|Val|Leu|
| | |130| | | |135| | | |140| | | | |
|Lys|Lys|Tyr|Leu|Lys|Val|Asp|Val|Pro|Ser|Tyr|Glu|Gly|Ile|Phe|Gly|
|145| | | | |150| | | |155| | | | | |160|
|Lys|Gly|Arg|Asp|Lys|Lys|Ile|Glu|Glu|Ile|Asp|Glu|Asn|Ile|Leu|
| | | | |165| | | |170| | | | |175| |
|Ala|Asp|Tyr|Ile|Cys|Ser|Arg|Cys|Val|Tyr|Leu|Phe|Asp|Leu|Lys|Glu|
| | | |180| | | |185| | | | |190| | | |
|Lys|Leu|Met|Asn|Phe|Ile|Glu|Glu|Met|Asp|Met|Lys|Lys|Leu|Leu|Leu|
| | |195| | | | |200| | | |205| | | | |
|Glu|Ile|Glu|Met|Pro|Leu|Val|Glu|Val|Leu|Lys|Ser|Met|Glu|Val|Ser|
| |210| | | | |215| | | |220| | | | | |
|Gly|Phe|Thr|Leu|Asp|Lys|Glu|Val|Leu|Lys|Glu|Leu|Ser|Gln|Lys|Ile|
|225| | | | |230| | | |235| | | | | |240|
|Asp|Asp|Arg|Ile|Gly|Glu|Ile|Leu|Asp|Lys|Ile|Tyr|Lys|Glu|Ala|Gly|
| | | | |245| | | |250| | | | |255| |
|Tyr|Gln|Phe|Asn|Val|Asn|Ser|Pro|Lys|Gln|Leu|Ser|Glu|Phe|Leu|Phe|
| | |260| | | |265| | | | |270| | | | |
|Glu|Lys|Leu|Asn|Leu|Pro|Val|Ile|Lys|Lys|Thr|Lys|Thr|Gly|Tyr|Ser|
| |275| | | | |280| | | | |285| | | | |
|Thr|Asp|Ser|Glu|Val|Leu|Glu|Gln|Leu|Val|Pro|Tyr|Asn|Asp|Ile|Val|
|290| | | | |295| | | | |300| | | | | |
|Ser|Asp|Ile|Ile|Glu|Tyr|Arg|Gln|Leu|Thr|Lys|Leu|Lys|Ser|Thr|Tyr|
|305| | | | |310| | | |315| | | | |320| |
|Ile|Asp|Gly|Phe|Leu|Pro|Leu|Met|Asp|Glu|Asn|Asn|Arg|Val|His|Ser|
| | | |325| | | | |330| | | | |335| | |
|Asn|Phe|Lys|Gln|Met|Val|Thr|Ala|Thr|Gly|Arg|Ile|Ser|Ser|Ser|Glu|
| | |340| | | | |345| | | | |350| | | |
|Ala|Asn|Leu|Gln|Asn|Ile|Pro|Ile|Arg|Glu|Glu|Phe|Gly|Arg|Gln|Ile|
| |355| | | | |360| | | | |365| | | | |
|Arg|Arg|Ala|Phe|Ile|Pro|Arg|Ser|Arg|Asp|Gly|Tyr|Ile|Val|Ser|Ala|
|370| | | | |375| | | | |380| | | | | |
|Asp|Tyr|Ser|Gln|Ile|Glu|Leu|Arg|Val|Leu|Ala|His|Val|Ser|Gly|Asp|
|385| | | | |390| | | | |395| | | | |400|
|Glu|Lys|Leu|Ile|Glu|Ser|Phe|Met|Asn|Asn|Glu|Asp|Ile|His|Leu|Arg|
| | | |405| | | | |410| | | | |415| | |
|Thr|Ala|Ser|Glu|Val|Phe|Lys|Val|Pro|Met|Glu|Lys|Val|Thr|Pro|Glu|
| | |420| | | |425| | | | |430| | | | |
|Met|Arg|Arg|Ala|Ala|Lys|Ala|Val|Asn|Phe|Gly|Ile|Ile|Tyr|Gly|Ile|
| |435| | | | |440| | | | |445| | | | |
|Ser|Asp|Tyr|Gly|Leu|Ser|Arg|Asp|Leu|Lys|Ile|Ser|Arg|Lys|Glu|Ala|
|450| | | | |455| | | | |460| | | | | |
|Lys|Glu|Tyr|Ile|Asn|Asn|Tyr|Phe|Glu|Arg|Tyr|Lys|Gly|Val|Lys|Asp|
|465| | | | |470| | | | |475| | | | |480|
|Tyr|Ile|Glu|Lys|Ile|Val|Arg|Phe|Ala|Lys|Glu|Asn|Gly|Tyr|Val|Thr|
| | | |485| | | | |490| | | | |495| |
|Thr|Ile|Met|Asn|Arg|Arg|Arg|Tyr|Ile|Pro|Glu|Ile|Asn|Ser|Arg|Asn|

|     |     |     |     | 500 |     |     |     | 505 |     |     |     | 510 |     |     |
| --- | --- | --- | --- | --- | --- | --- | --- | --- | --- | --- | --- | --- | --- | --- |
| Phe | Thr | Gln | Arg | Ser | Gln | Ala | Glu | Arg | Leu | Ala | Met | Asn | Ala | Pro | Ile |
|     |     | 515 |     |     |     | 520 |     |     |     | 525 |     |     |     |     |     |
| Gln | Gly | Ser | Ala | Ala | Asp | Ile | Ile | Lys | Met | Ala | Met | Val | Lys | Val | Tyr |
|     | 530 |     |     |     |     | 535 |     |     |     |     | 540 |     |     |     |     |
| Asn | Asp | Leu | Lys | Lys | Leu | Lys | Leu | Lys | Ser | Lys | Leu | Ile | Leu | Gln | Val |
| 545 |     |     |     |     | 550 |     |     |     |     | 555 |     |     |     |     | 560 |
| His | Asp | Glu | Leu | Val | Val | Asp | Thr | Tyr | Lys | Asp | Glu | Val | Asp | Ile | Ile |
|     |     |     |     | 565 |     |     |     |     | 570 |     |     |     |     | 575 |     |
| Lys | Lys | Ile | Leu | Lys | Glu | Asn | Met | Glu | Asn | Val | Val | Gln | Leu | Lys | Val |
|     |     |     | 580 |     |     |     |     | 585 |     |     |     |     | 590 |     |     |
| Pro | Leu | Val | Val | Glu | Ile | Gly | Val | Gly | Pro | Asn | Trp | Phe | Leu | Ala | Lys |
|     |     | 595 |     |     |     |     | 600 |     |     |     |     | 605 |     |     |     |

( 2 ) INFORMATION FOR SEQ ID NO: 4:

( i ) SEQUENCE CHARACTERISTICS:
        ( A ) LENGTH: 578 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 4:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Lys | Val | Glu | Lys | Trp | Ser | Lys | Val | Asp | Ile | Lys | Glu | Leu | Val | Thr |
| 1   |     |     |     | 5   |     |     |     |     | 10  |     |     |     |     | 15  |     |
| Leu | Leu | Gln | Asp | Asn | Arg | Asn | Ile | Ala | Phe | Tyr | Pro | Leu | Ile | Tyr | Glu |
|     |     |     | 20  |     |     |     |     | 25  |     |     |     |     | 30  |     |     |
| Gly | Glu | Ile | Lys | Lys | Ile | Ala | Phe | Ser | Phe | Gly | Lys | Asp | Thr | Val | Tyr |
|     |     | 35  |     |     |     |     | 40  |     |     |     |     | 45  |     |     |     |
| Ile | Asp | Val | Phe | Gln | Thr | Glu | Asp | Leu | Lys | Glu | Ile | Phe | Glu | Lys | Glu |
|     | 50  |     |     |     |     | 55  |     |     |     |     | 60  |     |     |     |     |
| Asp | Phe | Glu | Phe | Thr | Thr | His | Glu | Ile | Lys | Asp | Phe | Leu | Val | Arg | Leu |
| 65  |     |     |     |     | 70  |     |     |     |     | 75  |     |     |     |     | 80  |
| Ser | Tyr | Lys | Gly | Ile | Glu | Cys | Lys | Ser | Lys | Tyr | Ile | Asp | Thr | Ala | Val |
|     |     |     |     | 85  |     |     |     |     | 90  |     |     |     |     | 95  |     |
| Met | Ala | Tyr | Leu | Leu | Asn | Pro | Ser | Glu | Ser | Asn | Tyr | Asp | Leu | Asp | Arg |
|     |     |     | 100 |     |     |     |     | 105 |     |     |     |     | 110 |     |     |
| Val | Leu | Lys | Lys | Tyr | Leu | Lys | Val | Asp | Val | Pro | Ser | Tyr | Glu | Gly | Ile |
|     |     | 115 |     |     |     |     | 120 |     |     |     |     | 125 |     |     |     |
| Phe | Gly | Lys | Gly | Arg | Asp | Lys | Lys | Ile | Glu | Glu | Ile | Asp | Glu | Asn |     |
|     | 130 |     |     |     |     | 135 |     |     |     |     | 140 |     |     |     |     |
| Ile | Leu | Ala | Asp | Tyr | Ile | Cys | Ser | Arg | Cys | Val | Tyr | Leu | Phe | Asp | Leu |
| 145 |     |     |     |     | 150 |     |     |     |     | 155 |     |     |     |     | 160 |
| Lys | Glu | Lys | Leu | Met | Asn | Phe | Ile | Glu | Glu | Met | Asp | Met | Lys | Lys | Leu |
|     |     |     |     | 165 |     |     |     |     | 170 |     |     |     |     | 175 |     |
| Leu | Leu | Glu | Ile | Glu | Met | Pro | Leu | Val | Glu | Val | Leu | Lys | Ser | Met | Glu |
|     |     |     | 180 |     |     |     |     | 185 |     |     |     |     | 190 |     |     |
| Val | Ser | Gly | Phe | Thr | Leu | Asp | Lys | Glu | Val | Leu | Lys | Glu | Leu | Ser | Gln |
|     |     | 195 |     |     |     |     | 200 |     |     |     |     | 205 |     |     |     |
| Lys | Ile | Asp | Asp | Arg | Ile | Gly | Glu | Ile | Leu | Asp | Lys | Ile | Tyr | Lys | Glu |
|     | 210 |     |     |     |     | 215 |     |     |     |     | 220 |     |     |     |     |
| Ala | Gly | Tyr | Gln | Phe | Asn | Val | Asn | Ser | Pro | Lys | Gln | Leu | Ser | Glu | Phe |
| 225 |     |     |     |     | 230 |     |     |     |     | 235 |     |     |     |     | 240 |
| Leu | Phe | Glu | Lys | Leu | Asn | Leu | Pro | Val | Ile | Lys | Lys | Thr | Lys | Thr | Gly |
|     |     |     |     | 245 |     |     |     |     | 250 |     |     |     |     | 255 |     |

| Tyr | Ser | Thr | Asp | Ser | Glu | Val | Leu | Glu | Gln | Leu | Val | Pro | Tyr | Asn | Asp |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |
| Ile | Val | Ser | Asp | Ile | Ile | Glu | Tyr | Arg | Gln | Leu | Thr | Lys | Leu | Lys | Ser |
|     |     | 275 |     |     |     |     | 280 |     |     |     |     | 285 |     |     |     |
| Thr | Tyr | Ile | Asp | Gly | Phe | Leu | Pro | Leu | Met | Asp | Glu | Asn | Asn | Arg | Val |
|     | 290 |     |     |     |     | 295 |     |     |     |     | 300 |     |     |     |     |
| His | Ser | Asn | Phe | Lys | Gln | Met | Val | Thr | Ala | Thr | Gly | Arg | Ile | Ser | Ser |
| 305 |     |     |     |     | 310 |     |     |     |     | 315 |     |     |     |     | 320 |
| Ser | Glu | Ala | Asn | Leu | Gln | Asn | Ile | Pro | Ile | Arg | Glu | Glu | Phe | Gly | Arg |
|     |     |     |     | 325 |     |     |     |     | 330 |     |     |     |     | 335 |     |
| Gln | Ile | Arg | Arg | Ala | Phe | Ile | Pro | Arg | Ser | Arg | Asp | Gly | Tyr | Ile | Val |
|     |     |     | 340 |     |     |     |     | 345 |     |     |     |     | 350 |     |     |
| Ser | Ala | Asp | Tyr | Ser | Gln | Ile | Glu | Leu | Arg | Val | Leu | Ala | His | Val | Ser |
|     |     |     | 355 |     |     |     |     | 360 |     |     |     |     | 365 |     |     |
| Gly | Asp | Glu | Lys | Leu | Ile | Glu | Ser | Phe | Met | Asn | Asn | Glu | Asp | Ile | His |
|     |     | 370 |     |     |     |     | 375 |     |     |     |     | 380 |     |     |     |
| Leu | Arg | Thr | Ala | Ser | Glu | Val | Phe | Lys | Val | Pro | Met | Glu | Lys | Val | Thr |
| 385 |     |     |     |     |     | 390 |     |     |     |     | 395 |     |     |     | 400 |
| Pro | Glu | Met | Arg | Arg | Ala | Ala | Lys | Ala | Val | Asn | Tyr | Gly | Ile | Ile | Tyr |
|     |     |     |     | 405 |     |     |     |     | 410 |     |     |     |     | 415 |     |
| Gly | Ile | Ser | Asp | Tyr | Gly | Leu | Ser | Arg | Asp | Leu | Lys | Ile | Ser | Arg | Lys |
|     |     |     | 420 |     |     |     |     |     | 425 |     |     |     |     | 430 |     |
| Glu | Ala | Lys | Glu | Tyr | Ile | Asn | Asn | Tyr | Phe | Glu | Arg | Tyr | Lys | Gly | Val |
|     |     | 435 |     |     |     |     | 440 |     |     |     |     |     | 445 |     |     |
| Lys | Asp | Tyr | Ile | Glu | Lys | Ile | Val | Arg | Phe | Ala | Lys | Glu | Asn | Gly | Tyr |
|     | 450 |     |     |     |     | 455 |     |     |     |     | 460 |     |     |     |     |
| Val | Thr | Thr | Ile | Met | Asn | Arg | Arg | Arg | Tyr | Ile | Pro | Glu | Ile | Asn | Ser |
| 465 |     |     |     |     | 470 |     |     |     |     | 475 |     |     |     |     | 480 |
| Arg | Asn | Phe | Thr | Gln | Arg | Ser | Gln | Ala | Glu | Arg | Leu | Ala | Met | Asn | Ala |
|     |     |     |     | 485 |     |     |     |     | 490 |     |     |     |     | 495 |     |
| Pro | Ile | Gln | Gly | Ser | Ala | Ala | Asp | Ile | Ile | Lys | Met | Ala | Met | Val | Lys |
|     |     |     |     | 500 |     |     |     | 505 |     |     |     |     | 510 |     |     |
| Val | Tyr | Asn | Asp | Leu | Lys | Lys | Leu | Lys | Leu | Lys | Ser | Lys | Leu | Ile | Leu |
|     |     |     | 515 |     |     |     |     | 520 |     |     |     | 525 |     |     |     |
| Gln | Val | His | Asp | Glu | Leu | Val | Val | Asp | Thr | Tyr | Lys | Asp | Glu | Val | Asp |
|     |     | 530 |     |     |     |     | 535 |     |     |     |     | 540 |     |     |     |
| Ile | Ile | Lys | Lys | Ile | Leu | Lys | Glu | Asn | Met | Glu | Asn | Val | Val | Gln | Leu |
| 545 |     |     |     |     | 550 |     |     |     |     | 555 |     |     |     |     | 560 |
| Lys | Val | Pro | Leu | Val | Val | Glu | Ile | Gly | Val | Gly | Pro | Asn | Trp | Phe | Leu |
|     |     |     |     | 565 |     |     |     |     | 570 |     |     |     | 575 |     |     |
| Ala | Lys |     |     |     |     |     |     |     |     |     |     |     |     |     |     |

( 2 ) INFORMATION FOR SEQ ID NO: 5:

( i ) SEQUENCE CHARACTERISTICS:
       ( A ) LENGTH: 30 base pairs
       ( B ) TYPE: nucleic acid
       ( C ) STRANDEDNESS: single
       ( D ) TOPOLOGY: linear ( x i ) SEQUENCE DESCRIPTION: SEQ ID NO: 5:

GGTTCCCAAC GATCAAGGCG AGTTACATGA                                    30

( 2 ) INFORMATION FOR SEQ ID NO: 6:

( i ) SEQUENCE CHARACTERISTICS:

(A) LENGTH: 30 base pairs
(B) TYPE: nucleic acid
(C) STRANDEDNESS: single
(D) TOPOLOGY: linear (x i) SEQUENCE DESCRIPTION: SEQ ID NO: 6:

TCCCCCATGT TGTGCAAAAA AGCGGTTAGC 30

(2) INFORMATION FOR SEQ ID NO: 7:

(i) SEQUENCE CHARACTERISTICS:
(A) LENGTH: 23 base pairs
(B) TYPE: nucleic acid
(C) STRANDEDNESS: single
(D) TOPOLOGY: linear (i x) FEATURE:
(D) OTHER INFORMATION: "H"is A, T or C; "Y"is C or T;
"S"is C or G; and "R"is A or G.

(x i) SEQUENCE DESCRIPTION: SEQ ID NO: 7:

GACCCHAACY TSCARAAYAT HCC 23

(2) INFORMATION FOR SEQ ID NO: 8:

(i) SEQUENCE CHARACTERISTICS:
(A) LENGTH: 21 base pairs
(B) TYPE: nucleic acid
(C) STRANDEDNESS: single
(D) TOPOLOGY: linear (i x) FEATURE:
(D) OTHER INFORMATION: "K"is G or T; "S"is C or G;
"Y"is C or T; "R"is A or G; and
"N"is G, A, T or C.

(x i) SEQUENCE DESCRIPTION: SEQ ID NO: 8:

KASSAKYTCR TCGTGNACYT G 21

(2) INFORMATION FOR SEQ ID NO: 9:

(i) SEQUENCE CHARACTERISTICS:
(A) LENGTH: 32 base pairs
(B) TYPE: nucleic acid
(C) STRANDEDNESS: single
(D) TOPOLOGY: linear (x i) SEQUENCE DESCRIPTION: SEQ ID NO: 9:

GGGGTACCTC TAGATCACTT GGCCAAAAAC CA 32

(2) INFORMATION FOR SEQ ID NO: 10:

(i) SEQUENCE CHARACTERISTICS:
(A) LENGTH: 43 base pairs
(B) TYPE: nucleic acid
(C) STRANDEDNESS: single
(D) TOPOLOGY: linear (x i) SEQUENCE DESCRIPTION: SEQ ID NO: 10:

GGAATTCCAT ATGGCTTACC TGCTGAACCC GTCTGAGTCT AAC 43

(2) INFORMATION FOR SEQ ID NO: 11:

(i) SEQUENCE CHARACTERISTICS:
(A) LENGTH: 37 base pairs
(B) TYPE: nucleic acid
(C) STRANDEDNESS: single
(D) TOPOLOGY: linear (x i) SEQUENCE DESCRIPTION: SEQ ID NO: 11:

```
GGAATTCCAT ATGGCTCTTT CTTATAAAGG AATAGAG                                      37
```

( 2 ) INFORMATION FOR SEQ ID NO: 12:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 12:

```
GGAATTCCAT ATGAAAGTTG AAAAATGGTC A                                            31
```

( 2 ) INFORMATION FOR SEQ ID NO: 13:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 13:

```
GGAATTCCAT ATGAAAGTTG AAAAATGGTC TAAAGTAGAC ATCAAAGAAT TAG                    53
```

( 2 ) INFORMATION FOR SEQ ID NO: 14:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 14:

```
GGAATTCCAT ATGAAGCTTT TAGAGCTTTT                                              30
```

( 2 ) INFORMATION FOR SEQ ID NO: 15:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 15:

```
GGAATTCCAT ATGAAACTTT TAGAGCTTTT CAACAAATTA GAATTC                            46
```

( 2 ) INFORMATION FOR SEQ ID NO: 16:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 16:

```
CGATCGAGCA AGCCA                                                              15
```

( 2 ) INFORMATION FOR SEQ ID NO: 17:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 17:

```
CGAGCCGCTC GCTGA                                                              15
```

( 2 ) INFORMATION FOR SEQ ID NO: 18:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 18:

ACCGCATCGA ATGCATGTCT CGGGTAAGGC GTACTCGACC     40

( 2 ) INFORMATION FOR SEQ ID NO: 19:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 19:

CGATTCCGCT CCAGACTTCT CGGGTGTACT GAGATCCCCT     40

( 2 ) INFORMATION FOR SEQ ID NO: 20:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( D ) OTHER INFORMATION: "Xaa" is any amino acid.

( x i ) SEQUENCE DESCRIPTION: SEQ ID NO: 20:

Arg Xaa Xaa Xaa Lys Xaa Xaa Xaa Phe Xaa Xaa Xaa Tyr Gly
 1               5                   10

( 2 ) INFORMATION FOR SEQ ID NO: 21:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 21:

Arg Arg Ala Ala Lys Ala Val Asn Phe Gly Ile Ile Tyr Gly
 1               5                   10

( 2 ) INFORMATION FOR SEQ ID NO: 22:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 22:

AAGGTCAGAA AGCCCATAAT CGCTTATGCC ATATATTATG CCATAATTTA CGGC     54

( 2 ) INFORMATION FOR SEQ ID NO: 23:

( i ) SEQUENCE CHARACTERISTICS:
    ( A ) LENGTH: 2622 base pairs (B) TYPE: nucleic acid
(C) STRANDEDNESS: single
(D) TOPOLOGY: linear (xi) SEQUENCE DESCRIPTION: SEQ ID NO: 23:

| | | | | | | |
|---|---|---|---|---|---|---|
| ATGGCTTATA | AATTTTTAAT | CATTGATGGT | AGTAGCCTCA | TGTACAGAGC | CTATTATGCC | 60 |
| TTGCCCATGC | TTACTACAAG | TGAGGGATTG | CCTACAAATG | CTCTGTATGG | TTTTACTATG | 120 |
| ATGCTTATAA | AACTTATCGA | GGAGGAAAAA | CCTGATTACA | TAGCTATTGC | TTTTGACAAA | 180 |
| AAAGCTCCTA | CTTTTAGACA | CAAAGAATAT | CAAGACTACA | AAGCTACAAG | ACAAGCTATG | 240 |
| CCTGAAGAAC | TTGCTGAACA | AGTAGACTAT | TTGAAAGAAA | TTATAGATGG | CTTTAATATA | 300 |
| AAGACATTAG | AATTAGAAGG | TTATGAAGCT | GATGACATTA | TAGGGACTAT | TTCAAAGCTG | 360 |
| GCAGAGGAAA | AAGGAATGGA | AGTGCTTGTA | GTTACAGGAG | ACAGAGATGC | TCTTCAATTA | 420 |
| GTTTCAGATA | AAGTGAAGAT | AAAAATTTCT | AAAAAGGGTA | TTACTCAGAT | GGAAGAGTTT | 480 |
| GACGAAAAGG | CTATTTTAGA | AAGGTATGGA | ATAACTCCTC | AGCAGTTTAT | AGATTTAAAA | 540 |
| GGGCTTATGG | GAGATAAATC | TGATAATATC | CCTGGAGTAC | CTAATATAGG | GGAAAAAACT | 600 |
| GCGATTAAGC | TATTAAGGA | TTTTGGAACA | ATTGAAAATT | TAATCCAAAA | TCTTCTCAG | 660 |
| CTTAAAGGTA | AATAAAAGA | AAATATAGAA | AACAATAAAG | AGTTAGCTAT | AATGAGTAAG | 720 |
| AGGCTTGCTA | CTATAAAAAG | AGACATTCCC | ATTGAGATAG | ATTTGAGGA | GTATAAAGTA | 780 |
| AAAAAATTTA | ATGAGGAGAA | GCTTTTAGAG | CTTTTTAATA | AATTAGAATT | CTTTAGTTTA | 840 |
| ATTGATAACA | TAAAGAAAGA | AAGTAGCATA | GAGATTGTAG | ATAATCATAA | AGTTGAAAAA | 900 |
| TGGTCAAAAG | TAGATATAAA | AGAATTAGTA | ACTTGTTGC | AAGATAACAG | AAATATTGCT | 960 |
| TTTTACCCGT | TAATTTATGA | AGGGGAAATA | AAAAAAATAG | CCTTTTCTTT | TGGAAAGGAT | 1020 |
| ACGGTTTATA | TTGACGTTTT | CCAAACAGAA | GATTAAAGG | AGATTTTTGA | AAAAGAAGAT | 1080 |
| TTTGAATTTA | CAACCCATGA | AATAAAGGAT | TTTTTAGTGA | GGCTTTCTTA | TAAAGGAATA | 1140 |
| GAGTGTAAAA | GCAAGTACAT | AGATACTGCT | GTAATGGCTT | ATCTTCTGAA | TCCTTCTGAG | 1200 |
| TCTAACTATG | ACTTAGACCG | TGTGCTAAAA | AAATATTTAA | AGGTAGATGT | GCCTTCTTAT | 1260 |
| GAAGGAATAT | TTGGCAAAGG | TAGGGATAAA | AAGAAAATTG | AAGAGATTGA | CGAAAACATA | 1320 |
| CTTGCTGATT | ATATTTGCAG | TAGATGTGTG | TATCTATTTG | ATTTAAAAGA | AAAGCTGATG | 1380 |
| AATTTTATTG | AAGAGATGGA | TATGAAAAAA | CTTCTATTAG | AAATAGAAAT | GCCTCTTGTA | 1440 |
| GAAGTTTTAA | AATCAATGGA | GGTAAGTGGT | TTTACATTGG | ATAAAGAAGT | TCTAAAAGAG | 1500 |
| CTTTCACAAA | AGATAGATGA | TAGAATAGGA | GAAATACTAG | ATAAAATTTA | TAAAGAGGCA | 1560 |
| GGATATCAAT | TTAATGTAAA | TTCACCTAAG | CAATTAAGTG | AATTTTTGTT | TGAAAAGTTA | 1620 |
| AACTTACCAG | TAATAAAGAA | AACAAAAACA | GGATACTCTA | CGGATTCTGA | AGTTTTGGAA | 1680 |
| CAATTGGTTC | CTTATAATGA | TATTGTCAGC | GATATAATAG | AGTATCGGCA | ACTTACAAAA | 1740 |
| CTTAAATCTA | CTTATATAGA | TGGATTTTTG | CCTCTTATGG | ATGAAAACAA | TAGAGTACAT | 1800 |
| TCTAATTTTA | AACAAATGGT | TACTGCTACA | GGTAGAATAA | GCAGCACCGA | GCCAAATCTA | 1860 |
| CAAAATATAC | CTATAAGAGA | AGAGTTTGGC | AGACAAATTA | GAAGGGCTTT | TATTCCGAGG | 1920 |
| AGTAGAGATG | GATATATTGT | TTCAGCAGAT | TATTCTCAGA | TTGAACTGAG | GGTTTTAGCA | 1980 |
| CATGTTTCGG | GAGATGAAAA | GCTAATAGAA | TCTTTTATGA | ATAATGAAGA | TATACATTTA | 2040 |
| AGGACAGCTT | CGGAGGTTTT | TAAAGTTCCT | ATGGAAAAAG | TTACACCGGA | GATGAGAAGA | 2100 |
| GCAGCAAAAG | CCGTAAATTT | TGGCATAATA | TATGGCATAA | GCGATTATGG | GCTTTCTCGA | 2160 |
| GACCTTAAAA | TATCAAGAAA | AGAAGCAAAA | GAGTACATAA | ATAATTATTT | TGAAAGATAT | 2220 |

| AAAGGAGTAA | AAGATTATAT | TGAAAAAATA | GTACGATTTG | CAAAAGAAAA | TGGCTATGTG | 2280 |
| ACTACAATAA | TGAACAGAAG | GAGATATATT | CCTGAAATAA | ACTCAAGAAA | TTTTACTCAA | 2340 |
| AGATCGCAGG | CCGAAAGGTT | AGCAATGAAT | GCTCCGATAC | AGGGAAGTGC | GGCTGATATA | 2400 |
| ATAAAAATGG | CAATGGTTAA | GGTATACAAC | GATTTAAAAA | AATTAAAGCT | TAAGTCTAAG | 2460 |
| CTTATATTGC | AAGTTCATGA | CGAGCTTGTA | GTGGATACTT | ATAAGGATGA | AGTAGATATC | 2520 |
| ATAAAAAGA | TACTTAAAGA | AAATATGGAA | AATGTAGTGC | AATTAAAAGT | TCCTCTGGTT | 2580 |
| GTTGAAATTG | GCGTAGGGCC | TAATTGGTTT | TTGGCCAAGT | GA | | 2622 |

( 2 ) INFORMATION FOR SEQ ID NO: 24:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 24:

| GGAATTCCAT | ATGGCTTATA | AATTTTAAT | CATTGATGGT | AGTAGC | 46 |

( 2 ) INFORMATION FOR SEQ ID NO: 25:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 25:

| TCAGTGGTAT | TTGTGAGCCA | GGGCATTGGC | CACACCAGCC | ACCACCTTCT | 50 |

( 2 ) INFORMATION FOR SEQ ID NO: 26:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 26:

| ATCCCCCAAA | ACAGACAGAA | TGGTGCATCT | GTCC | 34 |

( 2 ) INFORMATION FOR SEQ ID NO: 27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 27:

| GTTCTCCTGG | AAGGAGGTGC | ACATGGCCTC | 30 |

( 2 ) INFORMATION FOR SEQ ID NO: 28:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 28:

| CACACAAGAG | TGAGATCGCC | CATCGGTTTA | AGGA | 34 |